(12) United States Patent
Daigle et al.

(10) Patent No.: US 10,914,826 B2
(45) Date of Patent: Feb. 9, 2021

(54) HIGH FRAME RATE QUANTITATIVE DOPPLER FLOW IMAGING USING UNFOCUSED TRANSMIT BEAMS

(75) Inventors: Ronald Elvin Daigle, Redmond, WA (US); Peter John Kaczkowski, Seattle, WA (US)

(73) Assignee: Verasonics, Inc., Kirkland, WA (US)

( * ) Notice: Subject to any disclaimer, the term of this patent is extended or adjusted under 35 U.S.C. 154(b) by 120 days.

(21) Appl. No.: 12/490,780

(22) Filed: Jun. 24, 2009

(65) Prior Publication Data

US 2009/0326379 A1 Dec. 31, 2009

Related U.S. Application Data

(60) Provisional application No. 61/076,057, filed on Jun. 26, 2008.

(51) Int. Cl.
*G01S 7/52* (2006.01)
*G01S 15/89* (2006.01)
(Continued)

(52) U.S. Cl.
CPC ............ *G01S 7/52028* (2013.01); *A61B 8/06* (2013.01); *A61B 8/13* (2013.01); *G01S 7/52034* (2013.01);
(Continued)

(58) Field of Classification Search
None
See application file for complete search history.

(56) References Cited

U.S. PATENT DOCUMENTS 5,365,929 A * 11/1994 Peterson ..................... 600/456
5,396,890 A    3/1995 Weng
(Continued)

FOREIGN PATENT DOCUMENTS

| CN | 101203183 A | 6/2008 |
|---|---|---|
| EP | 0 846 442 A2 | 6/1998 |
| EP | 1790384 A1 | 5/2007 |
| FR | 2848673 A1 | 6/2004 |

(Continued)

OTHER PUBLICATIONS

Taylor, L.S. et al., "Three-Dimesional Sonoelastography: Principles and Practices," Physics in Medicine and Biology 45:1477-1494, 2000.

(Continued)

*Primary Examiner* — Pascal M Bui Pho
*Assistant Examiner* — Marjan Saboktakin
(74) *Attorney, Agent, or Firm* — Seed Intellectual Property Law Group LLP

(57) ABSTRACT

An ultrasound imaging system with pixel oriented processing is provided in which a method of producing a Doppler velocity image is accomplished by emitting unfocused acoustic signals into a medium over substantially an entire field; receiving scattered and reflected ultrasonic signals on a transducer array in response to the emission; processing the received ultrasonic signals to extract information to construct a Doppler velocity signal corresponding to at least one point in the medium; and generating on a display device the Doppler velocity image from the processed Doppler velocity signal. Acquisition sequences and signal processing algorithms are described that provide improved quantification of fluid flow parameters, including improved discrimination between regions of blood flow and tissue. Very high frame rate Spectral Doppler and Vector Doppler acquisition modes for real-time and post-acquisition visualization over a large field of view are described.

56 Claims, 9 Drawing Sheets

(51) Int. Cl.
*A61B 8/13* (2006.01)
*A61B 8/06* (2006.01)

(52) U.S. Cl.
CPC ...... *G01S 7/52085* (2013.01); *G01S 15/8977* (2013.01); *G01S 15/8979* (2013.01); *G01S 7/52047* (2013.01); *G01S 15/8984* (2013.01); *G01S 15/8995* (2013.01)

(56) References Cited

U.S. PATENT DOCUMENTS

| | | | |
|---|---|---|---|
| 5,842,473 A | 12/1998 | Fenster et al. | |
| 5,910,119 A * | 6/1999 | Lin | 600/455 |
| 6,095,980 A * | 8/2000 | Burns et al. | 600/453 |
| 6,135,956 A | 10/2000 | Schmiesing et al. | |
| 6,234,968 B1 | 5/2001 | Sumanaweera et al. | |
| 6,468,213 B1 | 10/2002 | Knell et al. | |
| 6,551,246 B1 * | 4/2003 | Ustuner et al. | 600/447 |
| 6,569,102 B2 | 5/2003 | Imran et al. | |
| 6,618,206 B2 | 9/2003 | Tarakci et al. | |
| 6,620,103 B1 * | 9/2003 | Bruce | G01S 7/52038 600/455 |
| 6,663,567 B2 | 12/2003 | Ji et al. | |
| 6,685,645 B1 | 2/2004 | McLaughlin et al. | |
| 6,733,455 B2 | 5/2004 | Mo et al. | |
| 6,773,399 B2 | 8/2004 | Xi et al. | |
| 6,866,631 B2 | 3/2005 | McLaughlin et al. | |
| 6,866,632 B1 | 3/2005 | Chou et al. | |
| 7,984,651 B2 * | 7/2011 | Randall et al. | 73/661 |
| 8,287,456 B2 | 10/2012 | Daigle | |
| 2003/0028113 A1 | 2/2003 | Gilbert et al. | |
| 2004/0179332 A1 | 9/2004 | Smith et al. | |
| 2004/0254462 A1 * | 12/2004 | Kawagishi et al. | 600/437 |
| 2005/0049494 A1 | 3/2005 | Gritzky et al. | |
| 2005/0137479 A1 * | 6/2005 | Haider | 600/440 |
| 2006/0058661 A1 * | 3/2006 | Hirama | 600/437 |
| 2007/0016037 A1 | 1/2007 | Houle et al. | |
| 2009/0112095 A1 | 4/2009 | Daigle | |

FOREIGN PATENT DOCUMENTS

| | | |
|---|---|---|
| JP | 63-117739 A | 5/1988 |
| JP | 10-033535 A | 2/1998 |
| JP | 10-262975 A | 10/1998 |
| JP | 2005-028165 A | 2/2005 |
| JP | 2005-177494 A | 7/2005 |
| JP | 2006-000421 A | 1/2006 |
| JP | 2006-181058 A | 7/2006 |
| JP | 2008/110072 A | 5/2008 |
| WO | 2003093863 A1 | 11/2003 |
| WO | 2006/113445 A1 | 10/2006 |
| WO | 2006113445 A1 | 10/2006 |
| WO | 2008/065570 A1 | 6/2008 |
| WO | 2008/068709 A1 | 6/2008 |

OTHER PUBLICATIONS

Zong, X. et al., "Speckle Reduction and Contrast Enhancement of Echocardiograms via Multiscale Nonlinear Processing," IEEE Transactions on Medical Imaging 17(4):532-540, Aug. 1998.

* cited by examiner

Conventional Doppler Acquisition Sequence
and Image Space

Flow Velocity Vector Decomposed Into Axial
And Transverse Flow Components

HIGH FRAME RATE QUANTITATIVE DOPPLER FLOW IMAGING USING UNFOCUSED TRANSMIT BEAMS

BACKGROUND OF THE DISCLOSURE

Technical Field

The present disclosure is directed to a system and method of capturing and processing ultrasound data and generating images therefrom that represent fluid flow.

Description of the Related Art

Ultrasound Imaging has developed into an effective tool for diagnosing a wide variety of disease states and conditions. The market for ultrasound equipment has seen steady growth over the years, fueled by improvements in image quality and the capability to differentiate various types of tissue. Unfortunately, there are still many applications for ultrasound systems where the equipment costs are too high for significant adoption. Examples are application areas such as breast cancer detection, prostate imaging, musculoskeletal imaging, and interventional radiology. In these areas and others, the diagnostic efficacy of ultrasound imaging depends on excellent spatial and contrast resolution for differentiation and identification of various tissue types. These performance capabilities are found only on the more expensive ultrasound systems, which have more extensive processing capabilities.

Ultrasound imaging has always required extensive signal and image processing methods, especially for array systems employing as many as 128 or more transducer elements, each with unique signal processing requirements. The last decade has seen a transition to the improved accuracy and flexibility of digital signal processing in almost all systems except for those at the lowest tiers of the market. This transition has the potential for reducing system costs in the long term, by utilizing highly integrated digital circuitry. Unfortunately, the low manufacturing volumes of ultrasound systems results in substantial overhead and fixed costs for these unique circuits, and thus the transition to digital signal processing has not significantly reduced system cost.

Doppler methods in medical ultrasound encompass a number of related techniques for imaging and quantifying blood flow. For stationary targets, the round trip travel time of a pulse reflected from the target back to the transducer is the same for each transmission. Conversely, successive echographic returns from a moving object will arrive at different times with respect to the transmit pulse, and by cross correlating these echoes the velocity of the object can be estimated. Because the ultrasound path is directional (along the beam axis), only axial motion produces a Doppler signal. Flow that is transverse to the beam is not detectable, and thus the velocity magnitudes obtained in conventional Doppler methods represent only the axial component of the flow velocity vector. In order to estimate the true magnitude of the flow velocity vector, Vector Doppler methods are employed. Generally, these methods rely on multiple beam angle data to estimate the direction of the flow vector and the flow velocity vector.

Several Doppler-based methods have been developed to present different aspects of blood flow. Typically, "spatial imaging" of the flow field is used to locate vessels, to measure their size, and to observe flow structure. "Flow imaging" is used in conjunction with echographic imaging in a "duplex" mode that combines both types of images in an overlay, with echographic amplitude presented in grayscale and flow velocity rendered in color. The flow field is computed within a region of interest (ROI) that is a subset of the larger echographic image, because flow imaging is more demanding in both acquisition time and processing load.

Detailed quantification of flow velocity is possible within a much smaller sample volume chosen within the ROI. The smallest volume that can be sampled and processed independently is given by the axial length (the transmit pulse length) and the lateral beam widths (in and out of the imaging plane). Spatial resolution of any method depends on the size of the sample volume and also on the system sensitivity settings for that location.

The Spectral Doppler method reports the spectrum of flow velocity and how it varies over the cardiac cycle, and it usually presents the spectrum graphically as a spectrogram and audibly through loudspeakers. Moreover, the Spectral Doppler method computes the power spectrum of flow velocity obtained over a sequence of transmissions, and usually presents the spectrum graphically as a spectrogram and audibly through loudspeakers. Access to the full time-varying spectrum of blood velocities allows accurate calculation of mean and peak flow velocities within the sample region and provides the most complete characterization of flow disturbances of all the ultrasound Doppler methods.

Color Flow Doppler imaging of the velocity field within a region of interest is a method that presents flow using a color palette that typically renders higher velocities more brightly than slower ones, and distinguishes between different flow directions (generally toward the transducer or away from it) by using warm (reddish) and cool (bluish) tones. Very slowly moving and stationary regions are not colored, and a "wall filter" threshold is used to set the minimum cutoff velocity. Color Flow Doppler can provide approximate mean flow velocities in the region of interest, but accuracy is limited due to the short acquisition sequences needed to maintain reasonable frame rates.

Color Flow Doppler requires the acquisition of a rapid sequence of identical transmit-receive events, or "ensemble", to detect and quantify motion by various means, essentially looking for correlated differences in arrival time, or phase, of the signal. The pulse repetition frequency (PRF) can be as fast as permitted by the round trip travel time of sound from the transducer to the maximum depth of the image and back again, but is generally adjusted to the minimum permitted to visualize peak blood velocities without aliasing. Typically, an ensemble of between 8 and 16 pulse-echo events is used for each Doppler scan line in the ROI. Choice of transmit beam focus parameters usually leads to Doppler scan lines that are 2 to 3 times broader than those used for echographic imaging. The requirement to transmit an ensemble of pulses in each beam direction generally leads to slower frame rates for Color Flow Doppler than for echographic imaging. Artifacts from slow frame rate can often be more noticeable in Doppler imaging than in grayscale echography because significant changes in flow can occur over a fraction of a cardiac cycle, and even slight probe motion may result in apparent flow over the entire ROI.

Using a small ROI can improve frame rates, but may limit the assessment of flow abnormalities. For example, a Color Flow ROI using 10 Doppler lines and ensembles of 12 pulses requires 120 events, similar to a full frame echographic image.

In general, high quality Doppler imaging is more technically difficult than echographic imaging in great part because backscattering from blood is very weak compared to tissue. Well known fundamental challenges to producing uncluttered and artifact-free Color Flow images include:

- The requirement for highly repeatable transmit pulses, and very low noise and phase jitter in the acquisition hardware.
- Flow signals are often of the same order of magnitude as various sources of noise, but averaging has an adverse impact on frame rate and other motion artifacts.
- The large contrast between the scattering amplitudes of tissue and blood leads to difficulty in discriminating between vessel walls (strong echo) and moving blood (weak echo), even when the velocity contrast is high. In addition, blood flow velocity is often very slow near vessel walls, which often move (pulsate) in synchrony with the cardiac cycle.
- Doppler pulses are typically longer than echographic pulses, and care must be taken to spatially register the flow and echo images which have different resolutions. This is particularly challenging for small blood vessels since the sample volume for Doppler pulses can be larger than the vessel diameter.

BRIEF SUMMARY OF THE DISCLOSURE

Various approaches have been developed to address these problems, documented in both the technical literature and in prior patents. The embodiments described herein build on applicants' prior pixel-based processing of element-level ultrasound data that is the subject of co-pending U.S. patent application Ser. No. 11/911,633, and the use of unfocused transmit beams to elevate frame rate. The use of unfocused transmissions (for example, plane waves) is described for quantitative imaging using spectral Doppler processing. The disclosed embodiments describe new methods for real-time flow and motion quantification and for development of new imaging modes using post-processing of recorded high-PRF data.

In accordance with one embodiment, A method of producing a Doppler velocity image is provided, the method including: emitting unfocused acoustic signals into a medium over substantially an entire field; receiving scattered and reflected ultrasonic signals on a transducer array in response to the emission; processing the received ultrasonic signals to extract information to construct a Doppler velocity signal corresponding to at least one point in the medium; and generating on a display device the Doppler velocity image from the processed Doppler velocity signal.

In accordance with another embodiment of the disclosure, an ultrasound processing method is provided that includes: generating an unfocused acoustic signal; receiving scattered and reflected echoes of the unfocused acoustic signal at a plurality of receiving elements and obtaining a Doppler velocity echo signal therefrom; mapping given pixels into a region of the Doppler velocity echo signals; organizing the mapped region of the stored Doppler velocity echo signals into an array for the given pixels; processing the array to generate a signal response for the given pixels; and using the signal response to obtain Doppler velocity acoustic information for the given pixel.

In accordance with another aspect of the foregoing embodiment, the method includes an initial step of generating a set of given pixels chosen to represent an area in a field of view of the transducer generating the Doppler velocity acoustic signal, in which every given pixel in the set has a known spatial relationship to the plurality of receiving elements.

The disclosed embodiments of the present disclosure are also directed to an ultrasound imaging method and system that performs all signal processing and image formation in software executing on commercial CPUs. The only custom hardware required in this approach is for transmission of acoustic pulses and data acquisition and signal conditioning of the received signals from the transducer. As an important benefit, the new architecture allows improvements in system dynamic range that provide for utilization of new transducer materials in a low-cost scanhead design and new modes of acquisition that provide significant new diagnostic information.

The disclosed software-based ultrasound system architecture leverages the high volume, low cost processing technology from the computer industry by basing the design around a commercial computer motherboard. While some current ultrasound systems incorporate computer motherboards in their design, the computer is used only for the user interface and some system control and does not participate in any real-time processing tasks. In the disclosed architecture, the computer motherboard replaces almost all existing hardware, rather than complementing it. Basing the system in software on a general-purpose platform provides a flexible, high-performance imaging system at the lowest possible system cost. No custom integrated circuits are required for this approach, reducing system complexity and time-to-market. Moreover, as further improvements in CPU processing power are realized by the computer industry, they can be easily adopted by the system to enhance imaging performance or provide new modes of operation and information extraction.

In accordance with one embodiment of the pixel-oriented processing, the steps include generating an acoustic signal, receiving at least one echo of the acoustic signal at a plurality of receiving elements and obtaining an echo signal therefrom, storing each echo signal from each of the plurality of receiving elements, mapping a given pixel into a region of the stored echo signals, organizing the mapped region of the stored echo signals into an array for the given pixels, processing the array to generate a signal response for the given pixels, and using the signal response to obtain acoustic information for the given pixel.

In accordance with another aspect of the foregoing embodiment, an initial step is provided that includes generating a set of given pixels chosen to represent an area in a field of view of the transducer generating the acoustic signal, in which even given pixel in the array set has a known spatial relationship to the plurality of receiving elements. Preferably the method also includes generating an image from the acoustic information for the given pixels in the array.

In accordance with another aspect of the foregoing embodiment, the acoustic information can be used for one or more of the following, including, but not limited to, measuring and displaying spatial data, measuring and displaying temporal data, measuring and displaying blood flow data, and measuring and displaying tissue displacement responsive to induced mechanical displacement caused by an acoustic signal or acoustic transmit wave.

In accordance with another aspect of the foregoing embodiment, the method includes generating a plurality of acoustic signals, receiving echoes from the plurality of acoustic signals, combining the received echoes over multiple generating and receiving cycles to enhance acoustic information obtained therefrom.

In accordance with another aspect of the foregoing embodiment, the stored echo signals are combined and averaged. Furthermore, the signal response comprises an average of the stored echo signals.

In accordance with another aspect of the foregoing embodiment, the method includes combining results of multiple cycles of generating acoustic signals, receiving echoes, and obtaining echo signals from the received echoes to derive enhanced acoustic information.

In accordance with another aspect of the foregoing embodiment, the enhanced acoustic information includes spatial compounding that improves contrast resolution of a final image generated therefrom.

In accordance with another aspect of the foregoing embodiment, the combined signals are representative of Doppler information associated with moving tissue or moving blood cells.

In accordance with another aspect of the foregoing embodiment, the receiving, obtaining, and storing of echo signals is done at a rate that is higher than a rate of processing the array.

In accordance with another embodiment of the disclosure, an ultrasound processing method is provided that includes generating an acoustic signal, receiving at least one echo of the acoustic signal at a plurality of receiving elements and obtaining an echo signal therefrom, storing each echo signal from each of the plurality of receiving elements, mapping a given voxel into a region of the stored echo signals, organizing the mapped region of the stored echo signals into an array for the given voxel, processing the array to generate a signal response for the given voxel, and using the signal response to obtain three-dimensional acoustic information for the given voxel.

In accordance with another aspect of the foregoing embodiment, all of the aspects with respect to the first embodiment described above are applicable to this second embodiment of the disclosure.

In accordance with another embodiment of the disclosure, a method of processing acoustic echoes is provided that includes storing acoustic echo signals received from a plurality of receiving elements, mapping a given pixel into a region of the stored echo signals, organizing the mapped region of the stored echo signals into an array for the given pixel, performing operations on the array to generate a signal response for the given pixel, and using the signal response to obtain acoustic information for the given pixel.

In accordance with another embodiment of the disclosure, an ultrasound processing system is provided that includes a module adapted to generate an acoustic signal, receive at least one echo of the acoustic signal at a plurality of receiving elements in the module and obtain a plurality of echo signals therefrom, and means for processing that communicates with the module and is adapted to map a given pixel into a region of stored echo signals received from the module, to organize the mapped region of the stored echo signals into an array for the given pixel, to perform operations on the array to generate a signal response for the given pixel, and to use the signal response to obtain acoustic information for the given pixel.

In accordance with another aspect of the foregoing embodiment, the processing means is adapted to initially generate a set of given pixels in which each given pixel in the set has a known spatial relationship to a receiving element in the module. Ideally, the processing means is configured to generate an image from the acoustic information for the given pixels in the array. Alternatively or in combination therewith, a means for displaying an image is provided that receives the signal response from the processing means for generating an image on a computer display or in printed form or in other forms known to those skilled in the art.

In accordance with another embodiment of the present disclosure, an ultrasound processing system is provided that includes a module adapted to generate an acoustic signal, receive at least one echo of the acoustic signal at a plurality of receiving elements in the module and obtain a plurality of echo signals therefrom, and means for processing that communicates with the module and is adapted to map a given voxel into a region of stored echo signals received from the module, to organize the mapped region of the stored echo signals into an array for the given voxel, to perform operations on the array to generate a signal response for the given voxel, and to use the signal response to obtain acoustic information for the given voxel.

In summary, the benefits of changing to a software-based ultrasound system architecture implemented on commercially available computing platforms include:

Significantly lower cost of hardware.

Lower development costs and faster time to market by avoiding lengthy design cycles for custom integrated circuits (ASICs).

Direct leveraging of cost/performance advances in computer technology.

Flexibility for development of many new processing approaches, in commercial and academic environments.

Increased diagnostic capability, based on image quality improvements, for cost sensitive application areas.

Increased utilization of ultrasound in specialty applications where cost has been a barrier to adoption.

BRIEF DESCRIPTION OF THE DRAWINGS

The foregoing and other features and advantages of the present disclosure will be more readily appreciated as the same become better understood from the following detailed description of the present disclosure when taken in conjunction with the following drawings, wherein.

DETAILED DESCRIPTION OF THE DISCLOSURE

Figure 1:
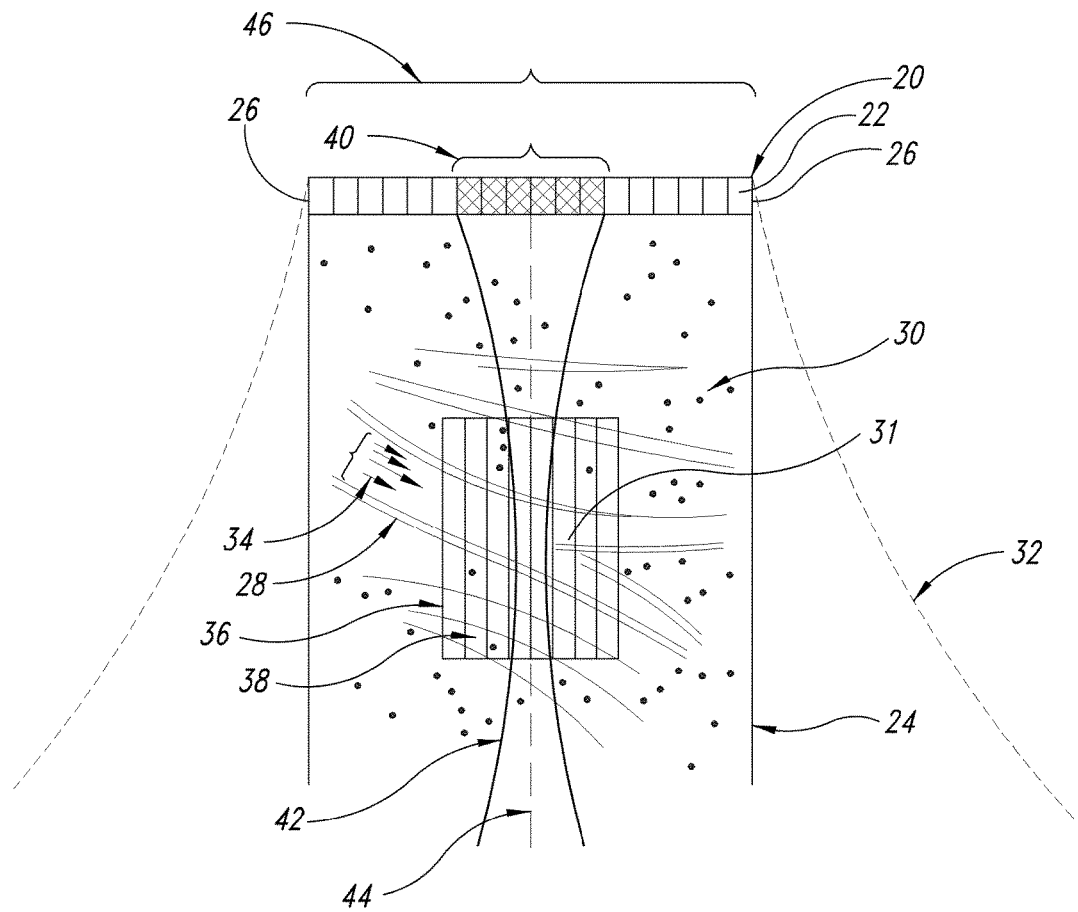
FIG. 1 illustrates a conventional Doppler acquisition sequence and image space.
Figure 1:
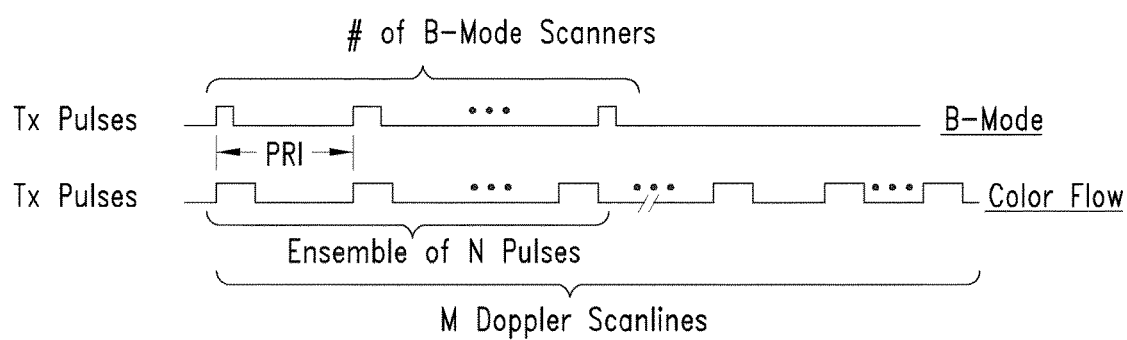

A conventional Doppler acquisition sequence and image scene are shown in FIG. 1 for a single beam direction that consists of an ensemble of N transmit-receive events (with 8≤N≤16). Conventional ultrasound systems form focused transmit beams and focus the received data dynamically, using delay-and-sum beam forming and several other processing steps required to form the image. In applicants' U.S. patent application Ser. No. 11/911,633, entitled "Ultrasound Imaging System with Pixel Oriented Processing," a method of image reconstruction is described below in conjunction with FIGS. 7-10 that greatly reduces the processing load compared to conventional beam forming and permits using a wide variety of non-conventional transmit fields.

For example, one non-conventional transmit field is the flat-focus transmit mode in which all transducer elements are fired in phase to produce a segment of a plane wave (for a linear array) that can be used to ensonify the entire field of view with a single pulse and thereby achieve extremely fast frame rates. The uniform phase transmit produces a flat focus or plane wave transmitted pulse for a linear array.

This is illustrated in FIG. 1 in which a transducer element or head 20 includes a plurality of individual transmitter/receivers 22 arranged as a linear array. The solid parallel lines extending from the sides of the transducer head 20 illustrate the two-dimensional nominal boundary 24 of energy that is emitted from the transducer head 20 towards a vessel 28 that is supported in tissue 30. The nominal boundary represents an imaging space of the linear array. A further two-dimensional boundary is shown by the dashed lines 32 that diverge as they extend from the sides 26 in the direction towards the vessel 28, representing the outer boundary of useful energy for imaging and Doppler use. As shown in FIG. 1, the vessel 28 carries fluid, indicated by the flow velocity vector arrows 34 that point generally towards the right of FIG. 1.

The particular region of interest (ROI) in FIG. 1 is defined by the rectangular box 36 in the center of the image, overlapping the center portion of the vessel 28 in which the vessel has a two-way branch 31. The ROI box 36 has parallel vertical lines 38 that are aligned with the ends of the respective transducer elements 20. To generate an image of the vessel 28 within the ROI, the transducer elements 20 that are aligned vertically with the ROI box 36 are selected for transmitting a beam. The selected transducer elements define a transmit sub-aperture 40 from which the focused transmit beam 42 is formed when the selected transmitters 22 are activated.

The shape of the transmit beam 42 is defined by the combined wave forms from each of the transmitters 22 in the transmit sub-aperture 40, which are centered around a longitudinal axis or nominal scan line 44. Backscattering of the transmit beam 42 results in reflected waves returning to all of the transmitter/receivers 22 in the transducer head 20, which in combination define the receive aperture 46, as shown in FIG. 1.

The operation of the sequence in B-mode is illustrated by the pulse plot at the bottom of FIG. 1 along with the plot of the ensemble of N pulses for color flow imaging. Because conventional B-mode and color flow imaging ensembles are well known to those skilled in the art, these will not be described in detail hereon. Briefly, each pulse shown on the pulse plots represents a pulse repetition on each scan line 38 separated by a pulse repetition interval (PRI). In color flow imaging, there are an ensemble of N pulses for each scan line 38.

In contrast to the focused transmit beam 42 shown in FIG. 1, a curvilinear array excited with uniform phase will produce a pulse with a curved wave front, producing a segment of a spherical wave appearing to emanate from the center of curvature of the array. This can also be accomplished by first activating the center transducers of a linear array followed sequentially by adjacent pairs of transducers progressively out to the end of the array.

A Doppler frame requiring an ensemble of N pulses can also be acquired at a frame rate of up to the maximum value permitted by the round trip travel time, which is given by PRF/N (typically, 1 kHz≤$PRF_{max}$≤12 kHz). The N data sets received during the ensemble are reconstructed using the pixel-based approach described below and further processed using conventional cross-correlation Doppler methods for (axial) flow velocity and power estimation over the entire field of view ensonified by the flat-focus transmitted field. The resulting Doppler frame rate is very fast, permitting acquisition (and processing) of a full-frame Doppler color flow image in the time it takes to produce a single conventional Doppler scan line. This is particularly useful in imaging of rapidly changing high-velocity flow. Furthermore, use of an acoustic plane wave will probe the flow field in a single direction, thus reducing the velocity spreading due to broad angle ensonification from a conventionally focused transmit beam.

Improved Measurement Accuracy

With the unfocused transmit Doppler imaging method, only a single Doppler ensemble acquisition is required for the entire frame. This allows the use of a much longer Doppler ensemble than is possible with the conventional multiple transmit beam approach while still supporting high frame rates. The conventional Doppler flow imaging methods utilize as many as 128 ensembles for a full frame flow image and thus must restrict maximum ensemble lengths to less than N=16 pulses in order to keep from significantly impacting frame rate. With the unfocused transmit Doppler method using only a single ensemble, the value of N can be many times greater than 16, while still allowing acquisition frame rates that are considerably higher than the conventional method. The longer unfocused transmit ensembles allow improved accuracy in the blood velocity estimate, since the uncertainty in the Doppler frequency estimate (from which is the blood velocity is derived) is on the order of the inverse of the total time of the ensemble.

For example, an ensemble length of 10 with a PRF of 5 KHz would have a total acquisition time of 2 milliseconds, resulting in a frequency uncertainty of 500 Hz. At a typical transducer frequency of 3 MHz, this would translate to a blood velocity uncertainty of around 13 cm/sec, a significant error for any attempt at blood flow quantification. Moreover, with a typical 64 ensemble conventional flow image combined with a 10 millisecond echo acquisition period, the frame rate for this example would be less than 8 frames per second. With the unfocused transmit Doppler method, an ensemble length of 100 pulses could be utilized, providing a 20 millisecond acquisition period and a blood velocity uncertainty of only 1.3 cm/sec. Again assuming a 10 millisecond acquisition period for the echo imaging portion of the frame, the frame rate is around 33 frames per second.

Multiple-Angle Unfocused-Transmit Doppler

As in the case of echographic imaging, the lack of focusing in the transmitted field leads to visibly larger side lobe interference (and thus poorer lateral resolution) than is achievable with focused transmit beams. It is well known that the combined beam pattern of a transmit-receive event is given by the product of transmit and receive beam patterns; and, since the flat-focus transmit has a uniform pattern, it offers no focal gain (hence no contribution to lateral resolution). The side lobe levels obtained using a plane wave transmit field can be greatly reduced by combining flat-focus ensembles for several different plane wave directions, that is, for plane waves emitted at different angles with respect to the transducer face. (Tilting the angle of the plane wave by phasing a linear array is equivalent to moving the apparent center of curvature of the curvilinear array and producing a synthetic array of point sources).

Because the flat-focus wavefronts remain nearly flat over the entire depth, the side lobe reduction is nearly uniform over the entire field of view. Even as few as five different plane wave angles combine to provide good side lobe reduction and lateral resolution throughout the image, and five ensembles can be acquired in less time than is typically required for a conventional Doppler color flow image frame that images flow inside a smaller ROI.

The method of the present disclosure utilizes an algorithm that adopts the multiple angle approach developed for gray-scale echographic imaging to collect the multiple-angle Doppler data. Since there are N pulses in each ensemble and M angles, the data can be collected in two ways: (a) collect all N pulses at one angle, and then change angles until all angles are complete or (b) collect one pulse for each of M angles and then repeat for N pulses. The choice is made based on the maximum expected flow velocity that, in turn, determines the requirements for the minimum PRF to avoid aliasing and other artifacts.

Figure 2:
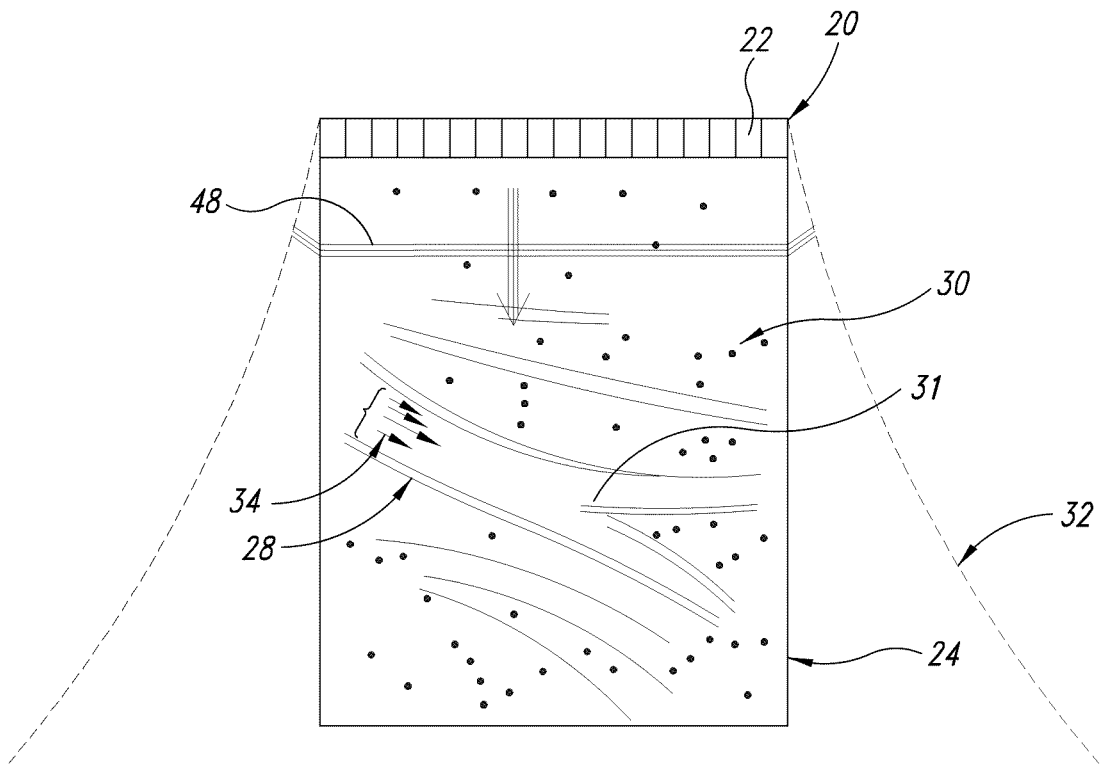
FIG. 2 illustrates a single angle unfocused transmit Doppler acquisition sequence and image space.

FIG. 2 illustrates the single angle unfocused linear Doppler sequence of the present disclosure. Here the transducer head 20 has all individual transducer elements 22 activated simultaneously, which generates an unfocused or "flat-focused" wavefront 48 into the tissue 30. The pulses plotted at the bottom of FIG. 2 illustrate in B mode a single or multiple angles and for the color mode the ensemble where M for the flat-focus is much greater than M for focused beams. The transducer head 20 receives the backscattered signals from the unfocused wavefront 48, sending the analog signals to a processor for storage and processing.

More particularly, once the data has been collected, the method proceeds to reconstruct an image from the ROI using one or more of at least two possible approaches. The first reconstructs multiple angle data for each pulse and then processes the ensemble of reconstructions using Doppler cross correlation. This approach produces best lateral resolution in the Doppler image, but does not preserve vector flow information, and produces spectral broadening much as focused transmit beams do in conventional systems. Alternatively, in a second approach the Doppler velocity and power can be estimated for each angle and then combined vectorially over each angle as described below. Combinations of the two processing approaches are also feasible.

Vector Doppler and Flow Detection

The fundamental reason for which conventional Doppler implementations provide only axial flow information is practical: the time required to cover the ROI with transmit beams (scan lines) in one direction is already at the limit of clinical utility. Adding beams at different transmit angles would not be possible without reducing frame rate and introducing artifacts and errors due to changing flow conditions and unintentional probe motion.

A new multiple-angle flat-focus Doppler approach can be used to obtain vector flow information at high frame rates because the entire flow field is probed using different transmit beams, each propagating in a unique direction. The data can be combined to estimate the flow direction and the flow velocity independently, by exploiting the known relationship between axial flow magnitude and the angle between the beam axis and the flow vector (Doppler angle). In addition, though noise will appear as flow in every ensemble, it is likely to be completely uncorrelated with angle. Thus, multiple-angle unfocused linear Doppler will provide both good lateral resolution and noise rejection using directional information. Of course, Vector Doppler information can also be used to provide a vectorial display of flow (e.g., streamline plots), and most importantly, the absolute velocity magnitude can be measured objectively, i.e., without ad-hoc angle correction, as long as flow is in the image plane. In this example, the image plane is in reference to the plane that intersects the scan lines 38 at a right angle. In the case of a linear array, the image plane would intersect at a right angle with a line projecting through the center of each transmitter-receiver 22 and perpendicular to its face. This plane represents the two dimensional region in space that is being imaged by the ultrasound system.

Figure 3:
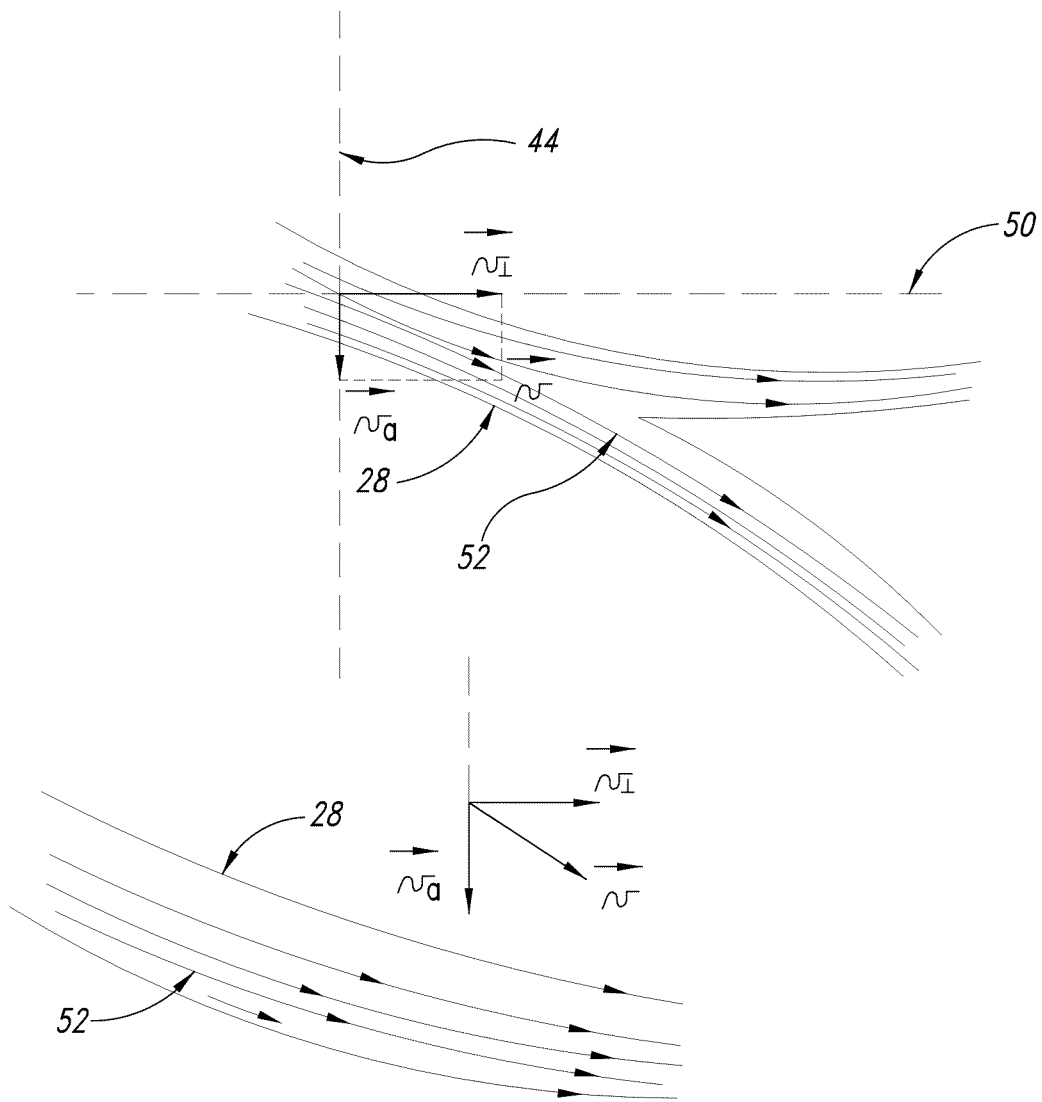
FIG. 3 illustrates a flow velocity vector decomposed into axial and transverse flow components.

FIG. 3 illustrates a flow vector that is decomposed into axial and transverse flow components. The vertical dashed line 44 is the axial direction of ultrasound transmission and the horizontal dashed line 50 is the transverse flow direction. Fluid flow within the vessel 28 is shown as elongated arrows 52.

Vector flow information must be preserved from the outset in order to take advantage of the ability to discriminate between noise and flow using multiple angle transmissions. Data collection may proceed along either scheme outlined for multiple angle acquisition. Processing steps outlined above can be combined in a matrix formulation such that a new processing algorithm treats the N×M matrix of Doppler data records together and improves lateral resolution, discriminates between tissue and flow regions, reduces noise, and provides vector flow information at fast frame rates.

Knowledge of both magnitude and direction of the flow velocity vector helps improve discrimination between true flow and noise, and between slow fluid flow and tissue that may also be in motion ('wall motion'). For example, slow flow signal magnitudes are often near the system noise floor, and a Doppler velocity magnitude threshold must be chosen sufficiently above the noise floor to prevent contamination of the flow display. The flow direction estimate is also noisy; however, the true flow direction is constant (over the small time interval used to make repeat measurements) whereas the noise direction is random with mean zero, and averaging several measurements reduces the noise and coherently combines the flow signals. Vector information also permits the use of other flow coherence filters that include neighboring sample volumes to improve SNR throughout the image.

It is well known that arteries often exhibit pulsatile motion that coincide with the cardiac cycle. Discrimination between wall motion and near-wall flow is improved by vector direction estimates because wall motion is primarily transverse to the vessel axis, whereas flow is generally longitudinal. Therefore, a sharp discontinuity in motion direction can be used to augment other means of discriminating between vessel wall and lumen.

Color Power Doppler

Conventional correlation processing produces estimates of Doppler velocity and Doppler power. The latter quantity is typically more sensitive to flow and can be used to detect and map small vessels. The noise reduction and lateral resolution enhancement benefits of multiple-angle flat-focus acquisition and vector processing extend to the Color Power Doppler mode as well.

There are numerous advantages to the embodiments described herein, including without limitation:

(a) Unfocused transmission Doppler flow imaging provides full frame flow images at high frame rates. A single ensemble is sufficient to measure flow over the entire image space, thus avoiding the process of ROI selection and tradeoff between Doppler region size and frame rate.

(b) The longer ensemble lengths that are realizable with the unfocused transmit Doppler method provide improved blood velocity measurement accuracy, without significant frame rate reduction.

(c) Single angle transmission (plane wave flat-focus using a linear transducer) provides narrow angle excitation, and reduces system-intrinsic spectral broadening.

(d) Multi-angle unfocused transmits, such as linear transmits, allow high frame rate Vector Doppler measurements over entire image.

(e) Multi-angle Doppler measurements allow improved discrimination between regions of flow and no flow, using various metrics (e.g., the variance of the velocity estimate, the Mean Squared Error of the angular fit of vector direction and amplitude, or the multi-angle estimate of Doppler power).

The method is extended to use a combination of unfocused transmit plane waves steered to propagate in different directions, and improve lateral resolution of the Color Flow image over the entire field of view. The method can be adapted to use a combination of unfocused transmit plane waves steered to propagate in different directions to obtain vector flow direction and magnitude over the entire field of view, and to do so with a standard transducer. The flow must be in the plane of the image to provide absolute flow magnitudes.

The method can also be adapted to use a combination of unfocused transmit plane waves steered to propagate in different directions to improve discrimination between true flow and noise, using the vectorial flow information referenced above and the relationship between Doppler angle and Doppler velocity magnitude. In addition, these methods can be adapted to curvilinear arrays (circular wavefronts, with apparent center of curvature displaced to create a synthetic array of point sources).

Transducer arrays of any general geometry, including "phased arrays" or "sector arrays", "spherical arrays", "2D arrays", can be adapted to produce linear, circular, plane, spherical, or other wavefronts that produce "angular diversity" in accordance with the embodiments of the present disclosure.

The embodiments of the present disclosure also extend to software implementation of pixel-based processing to include Doppler and Vector Doppler processing. This disclosure encompasses hardware implementation of pixel-based Doppler and Vector Doppler processing (e.g., FPGA, ASIC) as well as the use of hardware implementation of conventional receive beam forming processing to include and accommodate the use of plane wave and other unfocussed beams and acquisition sequences and processing approaches described herein. The foregoing also applies to Color Power Doppler processing.

High Frame Rate Full-Field Spectral Doppler

The conventional Spectral Doppler acquisition sequence for quantifying flow at a single image point may interleave three modes: (a) an echographic transmit-receive sequence 60, (b) a Color Flow ensemble 62 for color lines spanning a region of interest (ROI) within the echographic frame containing the image point, and (c) a longer high PRF sequence 64 using a single focused transmit beam shown in FIG. 4. Often referred to as "Triple Mode," this interleaving of the three acquisition modes 60, 62, 64 provides confidence that the targeted point remains in the intended location for flow quantification, and it also restricts the overall frame rate due to the significant amount of time required to acquire the information.

Figure 4:
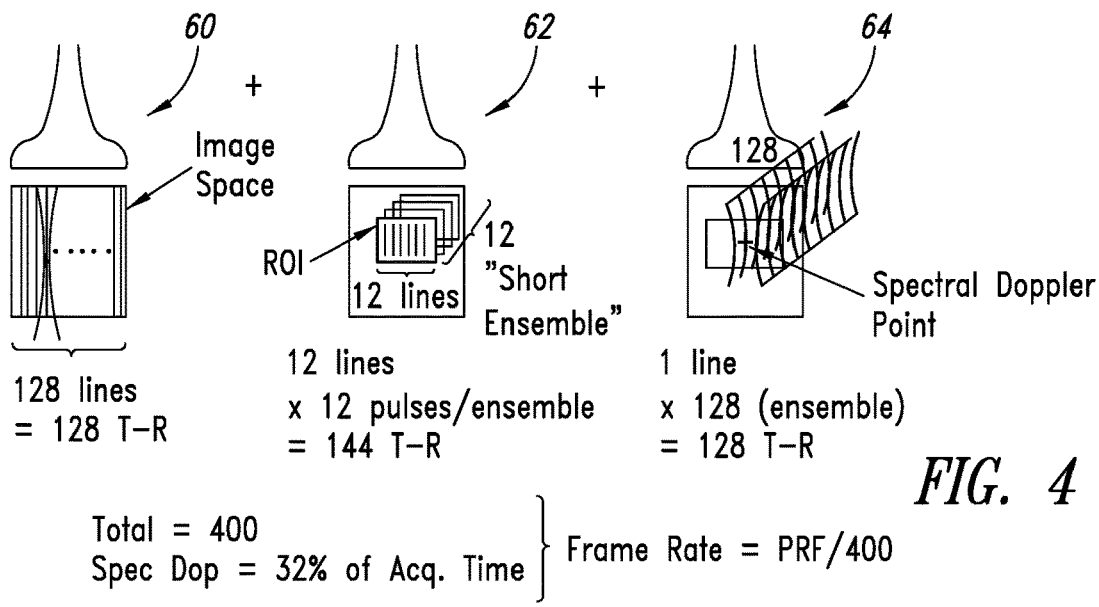
FIG. 4 illustrates the acquisition sequence for interleaving echography, color flow, and spectral Doppler imaging in a conventional ultrasound system.

Ultrasound systems currently in use all utilize focused transmit beams for triple mode scanning, such as shown in FIG. 1. This approach provides good sensitivity and spatial resolution, but it takes a considerable amount of time to scan a region of interest within the imaging field of the transducer. The application of plane wave transmit fields to triplex scanning permits very high frame rate imaging of both echographic and color flow modes, thus minimizing the overhead of acquisition time allocated to targeting the spectral Doppler. Furthermore, since targeting does not require image quality as good as that needed for diagnostic scans, it may not even be necessary to use multiple-angle plane wave sequences to improve image resolution and contrast. The triple mode imaging example of FIG. 4 is presented using unfocused plane wave transmissions in FIG. 5. Note that the spectral Doppler transmit beams may be tightly focused on the sample point for highest side lobe rejection, or may use an unfocused plane wave. The latter has the advantage of having a single Doppler angle (a focused beam has a spread of Doppler angles), but results in a slightly larger sample volume.

In the example shown in FIG. 4, 128 transmit-receive events are used for one frame of the echographic imaging process 60, 144 transmit-receive events are used for a Color Flow frame (ensemble length N=12) 62, and an ensemble of M=128 are used to obtain a Doppler spectrum 64. This spectrum is displayed as a column of pixels (not shown) in which the pixel brightness represents the Doppler power in that frequency (velocity) interval. In this example, the ratio of time allocated to Spectral Doppler is less than one third (32%) of the total frame acquisition time. A new spectrum is computed every frame and displayed as another vertical pixel band in a scrolling display.

Figure 5:
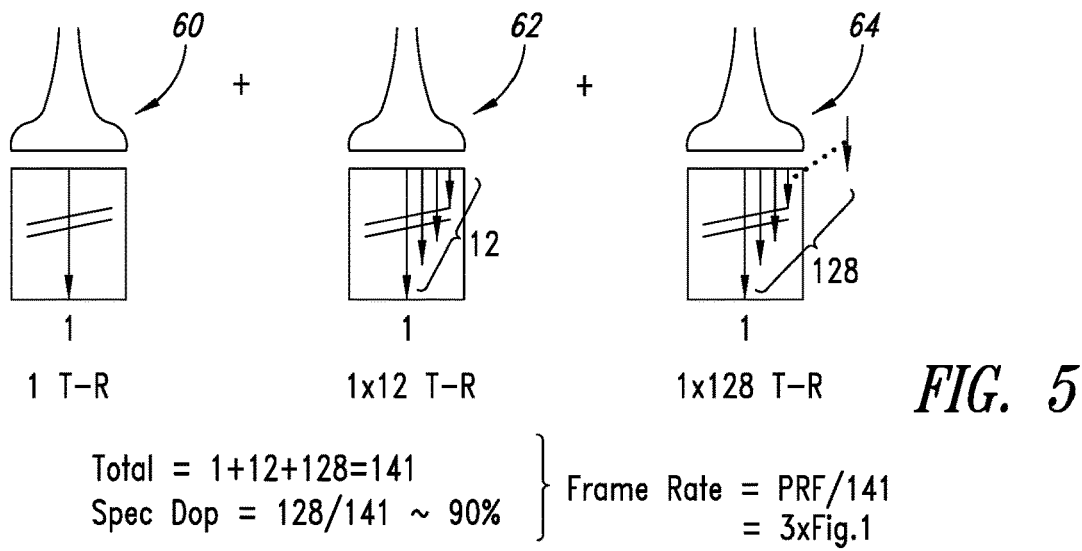
FIG. 5 illustrates the acquisition sequence for interleaving echography, color flow, and spectral Doppler imaging using unfocused plane wave transmission.

In FIG. 5, an acquisition sequence for interleaving Echography 60, Color Flow 62, and Spectral Doppler 64 methods using unfocused plane wave transmissions is illustrated. Replacing the focused transmits in the example of FIG. 4, only 1 transmit-receive event is needed for one frame of echographic imaging 60, one ensemble of 12 transmit-receive events is used for a Color Flow frame imaging 62, and 128 are used to obtain a Doppler spectrum image 64. The ratio of time allocated to spectral Doppler is 90% of the total.

Multiple-Point Spectral Doppler

The advantage inherent in using an unfocused transmit wave is that the entire echographic area can be ensonified at once, thus permitting the application of spectral Doppler processing to any of the points in the image space. Conventional systems that use multi-gate sampling may also provide spectra at several points, but these are restricted to points along the axis of a single beam line by practical considerations of adequate PRF and frame rate. The unfocused transmit permits quantitative comparisons between flows at multiple points anywhere in the image. Such comparisons can be made using complete spectra or for single spectral parameters (such as peak velocity) tracked over the cardiac cycle at any number of image points with no impact on acquisition PRF. Given the broad reach of the unfocused plane wave transmission, maintaining a fast PRF with real-time display of spectral parameters at multiple image points is limited only by the speed of data processing and display.

The ability to provide simultaneous quantitative flow information through spectral Doppler processing at multiple points in an ultrasound image with no compromise in PRF or image frame rate provides improved diagnosis of complex flow abnormalities with decreased examination times.

Focused transmit beams may be used to reduce side lobes. If the target points of interest lie near a single beam direction, an adaptive algorithm can automatically form a focused transmit beam that is no wider than necessary to ensonify the target points. Thus, the transmit beam can be tailored to reduce side lobe clutter while ensonifying the desired region. A user interface control may be provided to adjust the transmit beam width to assess the impact of the width on image quality in real time. If broad beam (weakly focused) ensonification is used, post-processing of the data may be performed to yield new flow visualizations not currently available, as discussed more fully below.

Post-Processing of Stored High-PRF Data

Storing a long sequence of high-PRF spectral data permits post-processing to quantify flow at any or all points in the ensonified region. For unfocused plane wave transmits, such post-processing would provide unprecedented quantitative flow and tissue motion images. A high-PRF data record extending over several cardiac cycles can be post-processed to produce color overlays of quantitative flow parameters that are derived from the spectral Doppler information. Spectral Doppler processing provides highly accurate flow information, in contrast to Color Doppler images where flow parameters are based on ensemble data.

Figure 6:
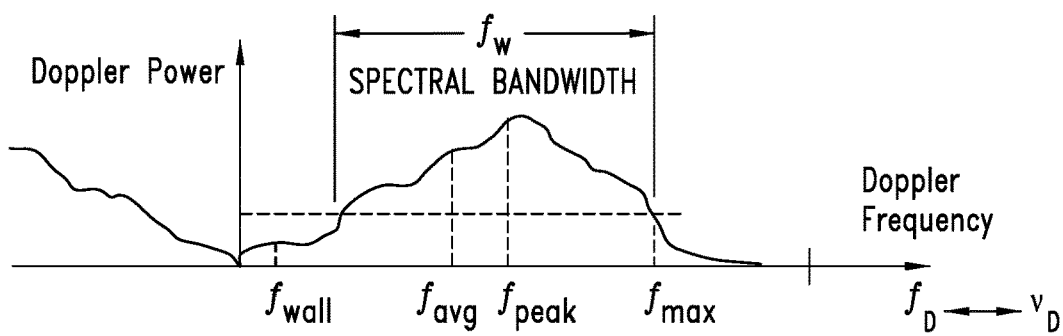
FIG. 6 illustrates the Doppler velocity power spectrum as a function of Doppler frequency or, equivalently, Doppler velocity.

In FIG. 6, several parameters of clinical interest obtained from the Doppler spectrum are diagrammed, and each of these could be computed for each image frame to create movies depicting different flow characteristics. For example, peak velocity, velocity corresponding to peak Doppler power, and integrated spectral power are each possible parameter choices for such new spectral Doppler movies. The Doppler velocity power spectrum is a function of Doppler frequency, or equivalently, Doppler velocity. The peak-power velocity is obtained by locating the mode of the power spectrum, and the mean velocity is likewise given by the first moment of the spectrum. The peak velocity is defined using a power threshold level, below which the velocity estimate is considered unreliable. Similarly, the spectral width is defined by the distance between velocities for which the power has dropped to some level (for example, 6 dB) below the peak power level. The wall filter cutoff is used to eliminate tissue motion from the display of blood flow.

Alternatively, a new kind of image representing a flow map over a full cardiac cycle could be displayed. For example, maximum flow velocity detected during one or more cardiac cycles may be computed and mapped, as could maximum spectral breadth (a possible indicator of turbulence). The clinical utility of such new modes is unknown, but is promising because the information currently only obtainable at a single point can now be produced over the entire flow region. Furthermore, the ability to analyze the data in ways that were not anticipated by the examining sonographer may be of interest to clinicians tasked with reviewing the data remotely or well after the exam took place. New examination and data recording protocols, as well as the establishment of new post-exam processing procedures are anticipated in this invention.

The hardware that implements the foregoing processes is unique in that it permits storing large amounts of very high-PRF received data, extending over several cardiac cycles. Maximum data rate is limited primarily by the capacity of the transfer rate over the PCIe bus. Current system data rates permit transfers as high as 1.5 GB/s for 64 channels of receive data, thus enabling continuous streaming of high-PRF Doppler ultrasound data. The maximum time over which continuous streaming data can be stored before it is over-written with new data is limited primarily by the size of the host computer memory.

Multiple point spectral Doppler processing can be performed in real time, providing quantitative flow information at various spatial points in the field of view, but current limitations in signal processing bandwidth may limit the number of points and/or types of information extracted. Storing the received data and using post-processing to generate the spectral Doppler information overcomes this processing limitation and can produce completely new image types of other spectral parameters as selected by the user.

Key Advantages of this Approach

Using unfocused transmit pulses, spectral Doppler data is available for every point in the image space with no PRF penalty from having to transmit multiple beams. Consequently, several image points can be selected using clinical criteria, and processed and compared for the same transmission events thereby minimizing acquisition artifacts from rapidly changing flow.

Unfocused transmission triple mode imaging (echography, Color Flow, spectral Doppler) provides full frame images and Doppler data at very high PRF. A single color flow ensemble is sufficient to image flow over the entire echographic image space, thus providing more time for spectral Doppler acquisition.

Single angle transmission (e.g., plane wave flat-focus using a linear transducer) provides narrow angle excitation, and reduces system-intrinsic spectral broadening.

The hardware is capable of storing large amounts of very high-PRF data extending over many cardiac cycles. Unfocused transmissions permit processing the data using spectral Doppler methods to obtain complete spectra at every point in the image space. Flow (and possibly also tissue motion) can then be quantified at each point using any one of a number of parameters characterizing the spectrum, or its variation over time. Images can be generated using any of these parameters for unprecedented flow quantification and representation.

An advantage of unfocused excitation and long records of high-PRF data is that retrospective analysis of the data can be done in ways that the sonographer did not anticipate during the exam, though data quality can be assured using real-time display. This ability to do flexible retrospective analysis has potential application to conventional clinical review of patient scans and to telemedicine.

All of the methods described here to detect and quantify flow can also be applied to characterization of tissue motion in response to cardiac or respiratory stimulus or in response to externally applied force.

Figure 7:
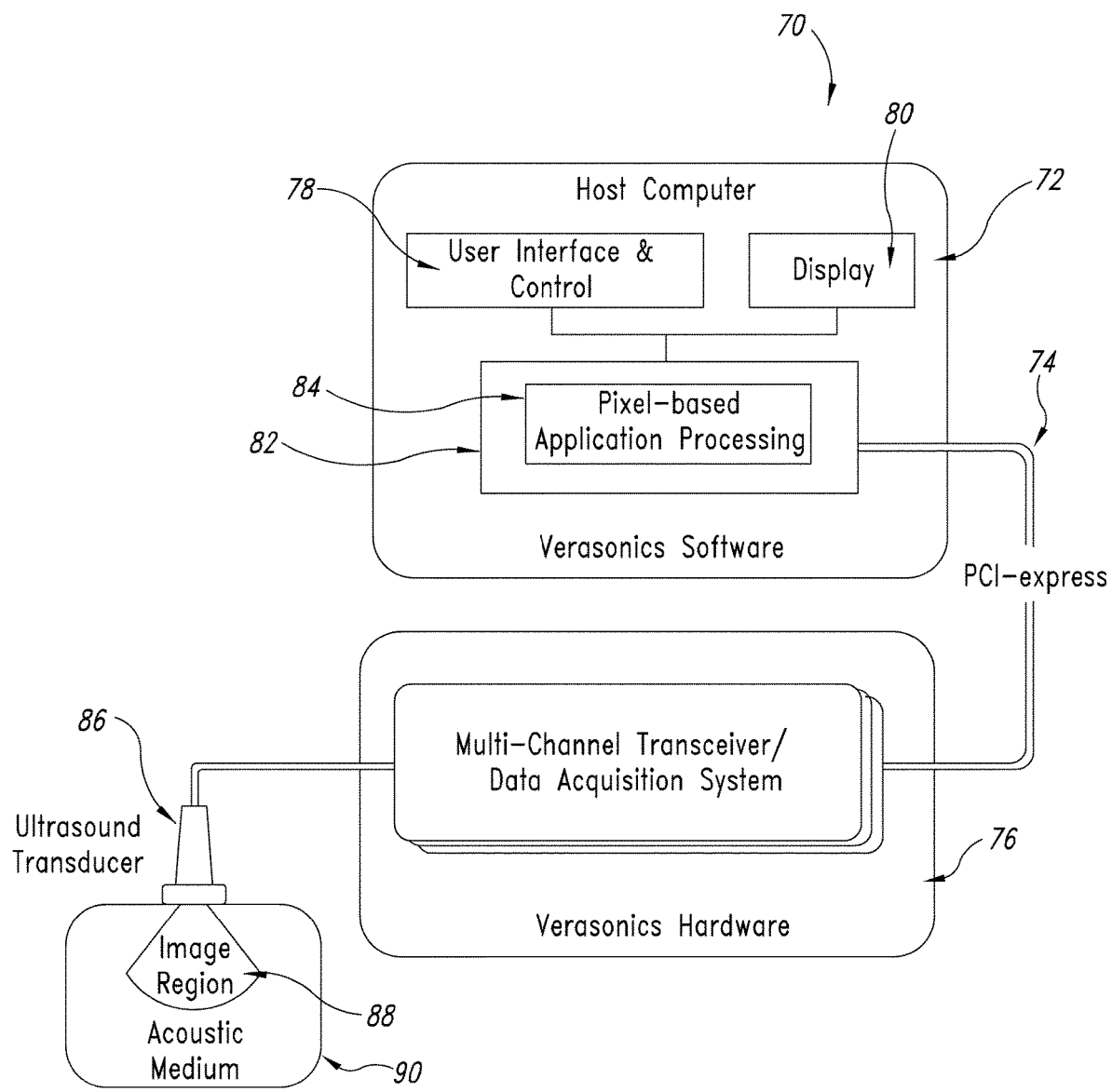
FIG. 7 illustrates a high-level representation of the system architecture for the processes of the present disclosure.
Figure 8:
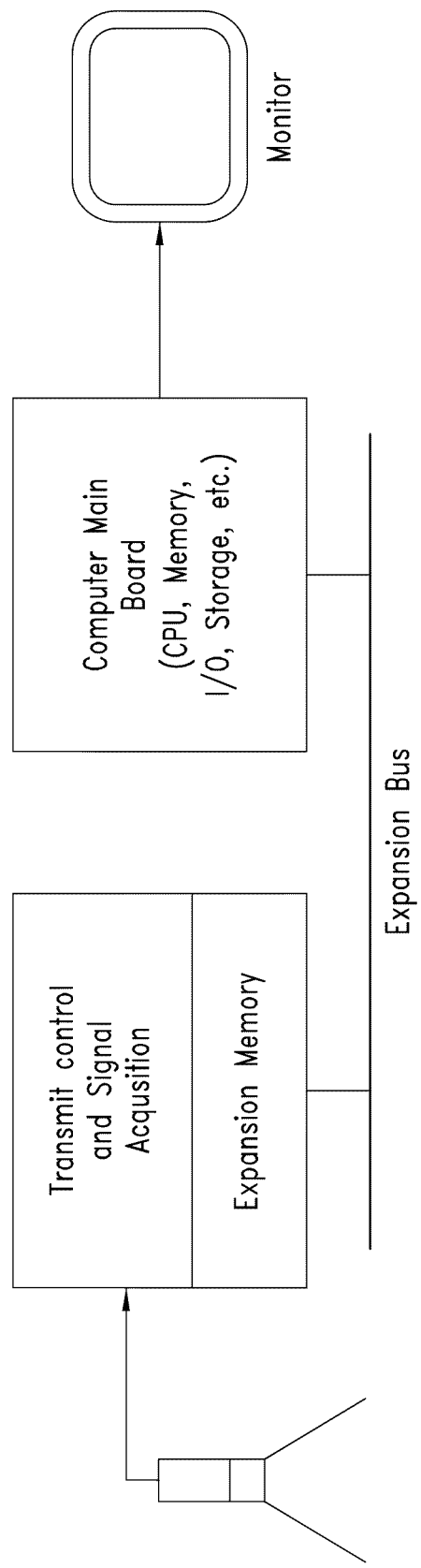
FIG. 8 is a schematic representation of a software-based architecture of one embodiment of pixel-oriented processing.

FIG. 7 is a system level block diagram that represents a high-level system architecture 70 for implementing the processes of the present disclosure. It is to be understood that this is merely one representative embodiment, and the illustrated architecture 70 is not a requirement for all embodiments of the present disclosure.

The architecture 70 includes a host computer 72 coupled via a PCI-express 74 to a multi-channel transceiver and data acquisition system 76. The host computer 72 has a user interface and control 78, and a display 80, both coupled to a processor 82 that utilizes the pixel-based application processing software 84. The multi-channel transceiver and data acquisition system 76 hardware are coupled to an ultrasound transducer 86 that is used to image a region 88 in an acoustic medium 90. Because these components are readily commercially available, they will not be described in detail herein.

Pixel Oriented Processing

The software-based method and system architecture in accordance with one embodiment of the present disclosure implements all real-time processing functions in software. The proposed architecture is shown schematically in FIG. 8.

The only custom hardware component in the software-based system is a plug-in module to the expansion bus of the computer that contains the pulse generation and signal acquisition circuitry, and a large block of expansion memory that is used to store signal data. The signal acquisition process consists of amplifying and digitizing the signals returned from each of the transducer elements following a transmit pulse. Typically, the only filtering of the signals prior to digitization, other than the natural band-pass filtering provided by the transducer itself, is low pass, anti-aliasing filtering for A/D conversion. The signals are sampled at a constant rate consistent with the frequencies involved, and the digitized data are stored in memory with minimal processing. The straight-forward design of the signal acquisition allows the circuitry to be implemented with off-the-shelf components in a relatively small amount of board area.

Figure 9:
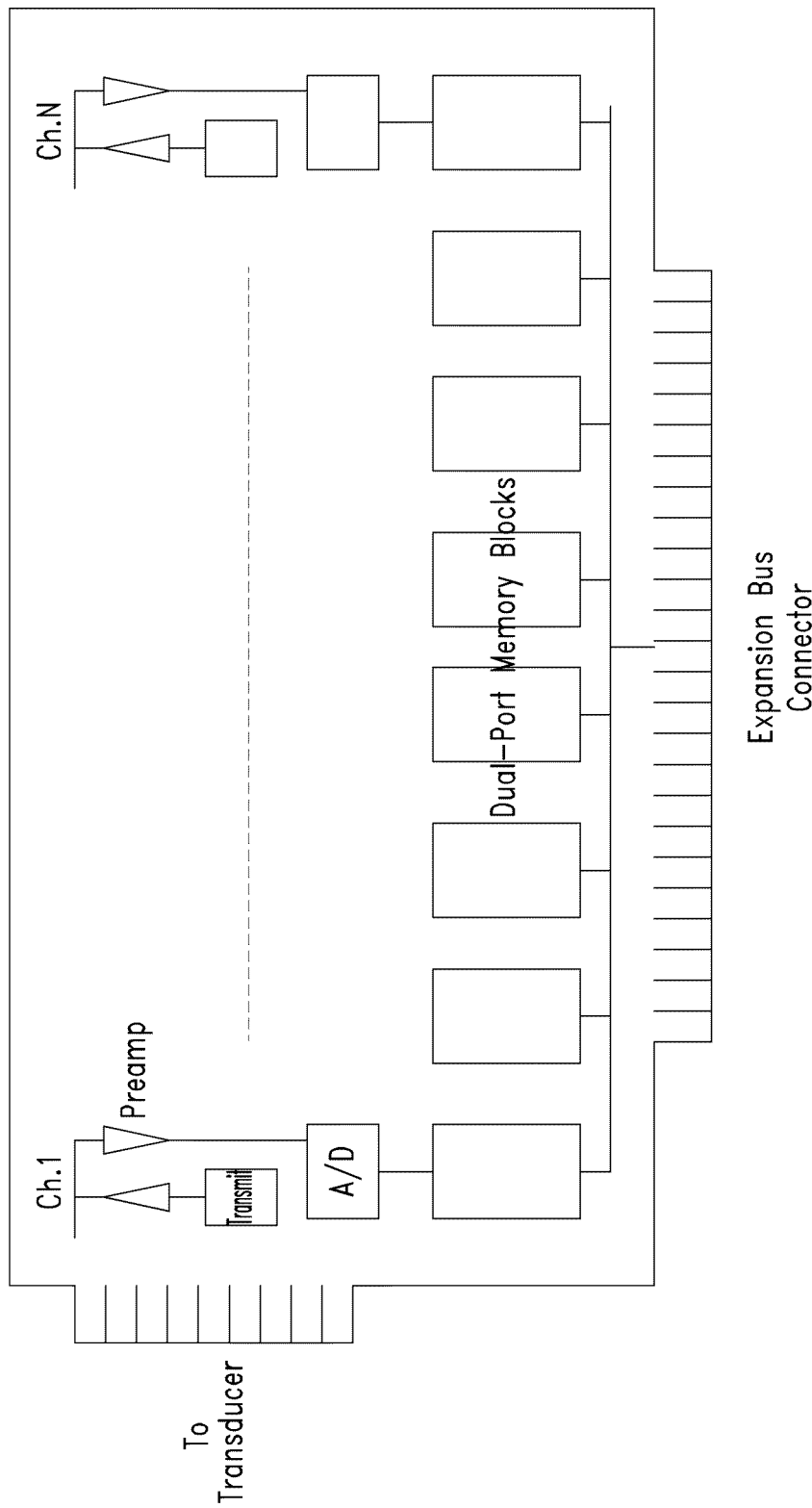
FIG. 9 is a diagram of a plug-in module formed in accordance with the pixel-oriented processing.

A more detailed look at the plug-in module is shown in FIG. 9. Multiple acquisition channels are shown, each composed of a transmitter, receiver pre-amplifier, A/D converter, and memory block. During receive, the transducer signals are digitized and written directly to the individual memory blocks. The memory blocks are dual-ported, meaning they can be read from the computer side at the same time acquisition data is being written from the A/D converter side. The memory blocks appear as normal expansion memory to the system CPU(s). It should be noted that the size of the plug-in module is not limited to the normal size of a standard computer expansion card, since the system is preferably housed in a custom enclosure. Also, multiple plug-in modules can be used to accommodate a large number of transducer elements, with each module processing a subset of the transducer aperture.

The components for the plug-in module, including amplifiers, A/D converters and associated interface circuitry, and the needed components for transmit pulse generation and signal acquisition are readily commercially available components and will not be described in detail herein. The memory block needed for RF data storage of echo signals obtained from received echoes is essentially the same circuitry as found in commercially available plug-in expansion memory cards, with the addition of a second direct memory access port for writing the digitized signal data. (The received echo signal data is generally referred to as RF data, since it consists of high frequency electrical oscillations generated by the transducer). The memory is mapped into the central processor's address space and can be accessed in a manner similar to other CPU memory located on the computer motherboard. The size of the memory is such that it can accommodate the individual channel receive data for up to 256 or more separate transmit/receive cycles. Since the maximum practical depth of penetration for round trip travel of an ultrasound pulse in the body is about 500 wavelengths, a typical sampling rate of four times the center frequency will require storage of as many as 4000 samples from an individual transducer element. For a sampling accuracy of 16 bits and 128 transducer channels, a maximum depth receive data acquisition will require approximately one megabyte of storage for each transmit/receive event. To store 256 events will therefore require 256 MB of storage, and all totaled, a 128 channel system could be built on a few plug-in cards.

Another aspect of the software-based ultrasound system is the computer motherboard and its associated components. The motherboard for the proposed design should preferably support a multi-processor CPU configuration, for obtaining the needed processing power. A complete multi-processor computer system, complete with power supply, memory, hard disk storage, DVD/CD-RW drive, and monitor is well-known to those skilled in the art, can be readily commercially purchased, and will not be described in greater detail.

A software-based ultrasound system must truly achieve "high-performance," meaning image quality comparable to existing high-end systems, in order to provide a significant benefit to the health care industry. This level of performance cannot be achieved by simply converting the flow-through processing methods of current systems to software implementations, since a simple addition of all the processing operations needed for one second of real-time imaging in the flow-through architecture gives a number that exceeds the typical number of operations per second currently achievable with several general purpose processors. Consequently, new processing methods are required that achieve a much greater efficiency than the flow-through methods.

Figure 10:
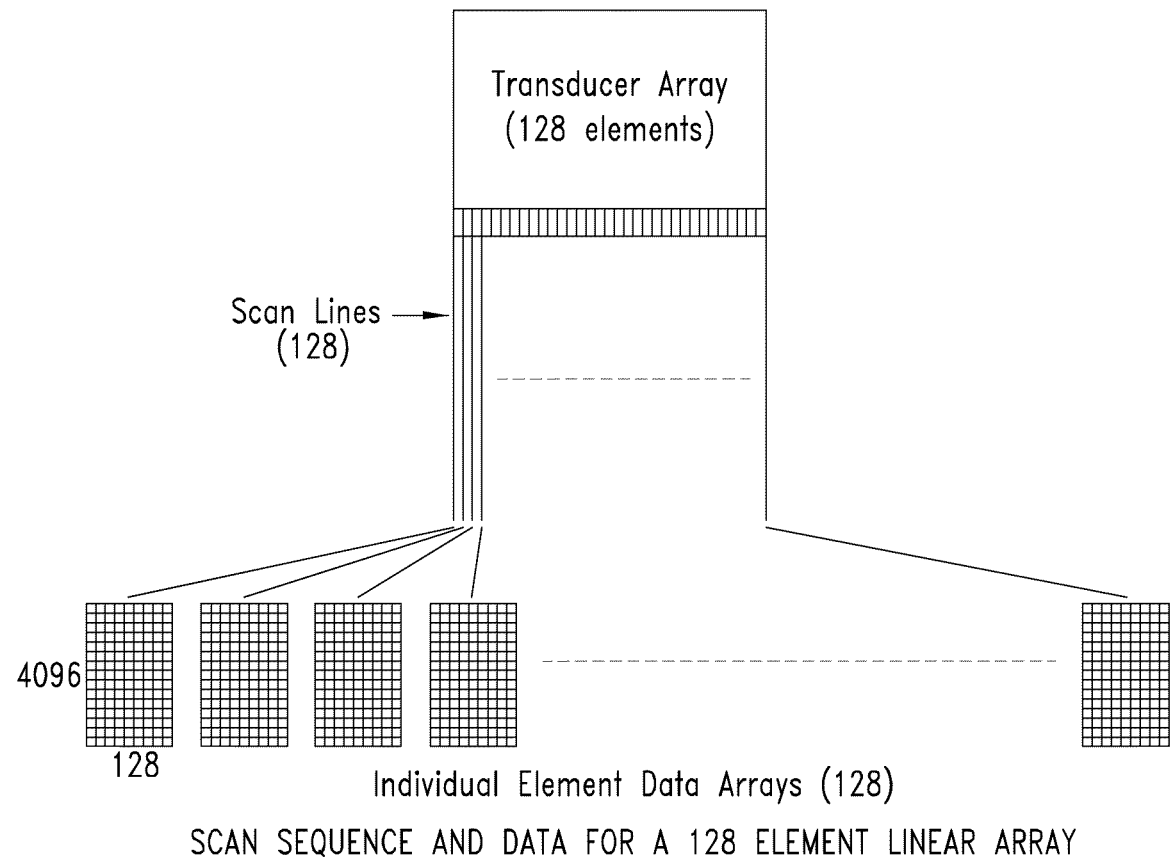
FIG. 10 is a schematic representation of the acquisition data for a 128 element linear array formed in accordance with the pixel-oriented processing.

In one embodiment of the software-based ultrasound system architecture of the present invention, the input data for signal and image processing consists of the set of RF samples acquired from individual transducer channels following one or more transmit events. For an example, let us consider a typical 2D imaging scanning mode with a 128 element linear transducer array, as shown in FIG. 10.

In this case, a 'transmit event' would consist of timed pulses from multiple transducer elements to generate a plurality of acoustic waves that combine in the media to form a focused ultrasound beam that emanates outwards from an origin point on the transducer at a specific element location. Multiple transmit events (128 in all) produce ultrasound beams that are sequentially emitted incrementally across the width of the transducer face, thus interrogating an entire image frame. For each of these transmit beams, the received echo data are collected from each of the 128 receiver elements in the transducer and organized into a data array with each column representing the sampled echo signal received by the corresponding transducer element. Thus, each array has 128 columns, corresponding to the 128 transducer elements, and a number of rows corresponding to the number of samples in depth that were taken (in this case, we will assume 4096 rows resulting in 4096 samples). These 128 data arrays then constitute an RF data set that is sufficient to produce one complete image frame.

It is worth noting that in the flow-through architecture, the RF data set described above does not even exist (at least not all at one time), since the beam and image formation takes place as the data streams in from the transducer. In other words, as the data return to each element after a transmit event, they are processed and combined (referred to as beam forming) to generate a single RF signal representing the focused return along a single beam (scan line). This RF signal is processed (again in real-time) into echo amplitude samples, which are stored in a memory array. When all beam directions have been processed, the echo amplitude data are then interpolated and formatted into a pixel image for display. Since all processing takes place in real-time, the processing circuitry must be able to 'keep up' with the data streaming in from the transducer elements.

In the software-based architecture of the present invention, all input data is stored prior to processing. This uncouples the acquisition rate from the processing rate, allowing the processing time to be longer than the acquisition time, if needed. This is a distinct advantage in high frequency scans, where the depth of acquisition is short and the sample rate high. For example, a 10 MHz scan head might have a useable depth of imaging of around four centimeters. In this case, the speed of sound in tissue dictates that each of the 128 transmit/receive events acquire and store their data in 52 microseconds, a very high acquisition data rate. In the flow-through architecture, these acquisition data would be formed into scan lines in real-time at high processing rates. In the software-based architecture of the present invention, the storage of RF data allows the processing to take as long as the frame period of the display, which for real-time visualization of tissue movement is typically 33 milliseconds (30 frames/second). For 128 pixel columns (the rough analogy to scan lines), this would allow 258 microseconds of processing time per column, rather than the 52 microseconds of the flow-through architecture. This storage strategy has the effect of substantially lowering the maximum rate of processing compared with the flow-through architecture for typical scan depths.

The storing of input data reduces the maximum processing rates but doesn't necessarily reduce the number of processing steps. To accomplish this, a new approach to ultrasound data processing is taken. The first step is to recognize that the ultimate goal of the system when in an imaging mode is to produce an image on the output display. An ultrasound image has a fundamental resolution that depends on the physical parameters of the acquisition system, such as the frequency and array dimensions, and can be represented as a rectangular array of pixel values that encode echo amplitude or some other tissue (acoustic) property. The density of this rectangular pixel array must provide adequate spatial sampling of the image resolution. It is recognized that display images need not consist only of rectangular arrays of pixels, but could consist of any arbitrary set of pixels, representing different geometric shapes. The next step is to start with one of the pixels in this image array and consider which sample points in the RF data set contribute to the calculation of this pixel's intensity, and determine the most efficient way of accessing and processing them. This approach is a completely different approach than the one utilized by the current flow-through architecture because only information that contributes to pixels on the display needs to be processed. In the approach of the present invention, a small region on the display image will take less overall processing time than a large image region, because the small region contains fewer pixels. In contrast, the flow-through processing methods must be designed to handle the maximum data stream bandwidths, independent of the image region size.

After processing the pixel array required to adequately represent the ultrasound image, the array can be rendered to the computer display at an appropriate size for viewing. The graphics processor of the computer, requiring no additional CPU processing, can typically carry out this operation, which consists of simple scaling and interpolation.

Figure 11:
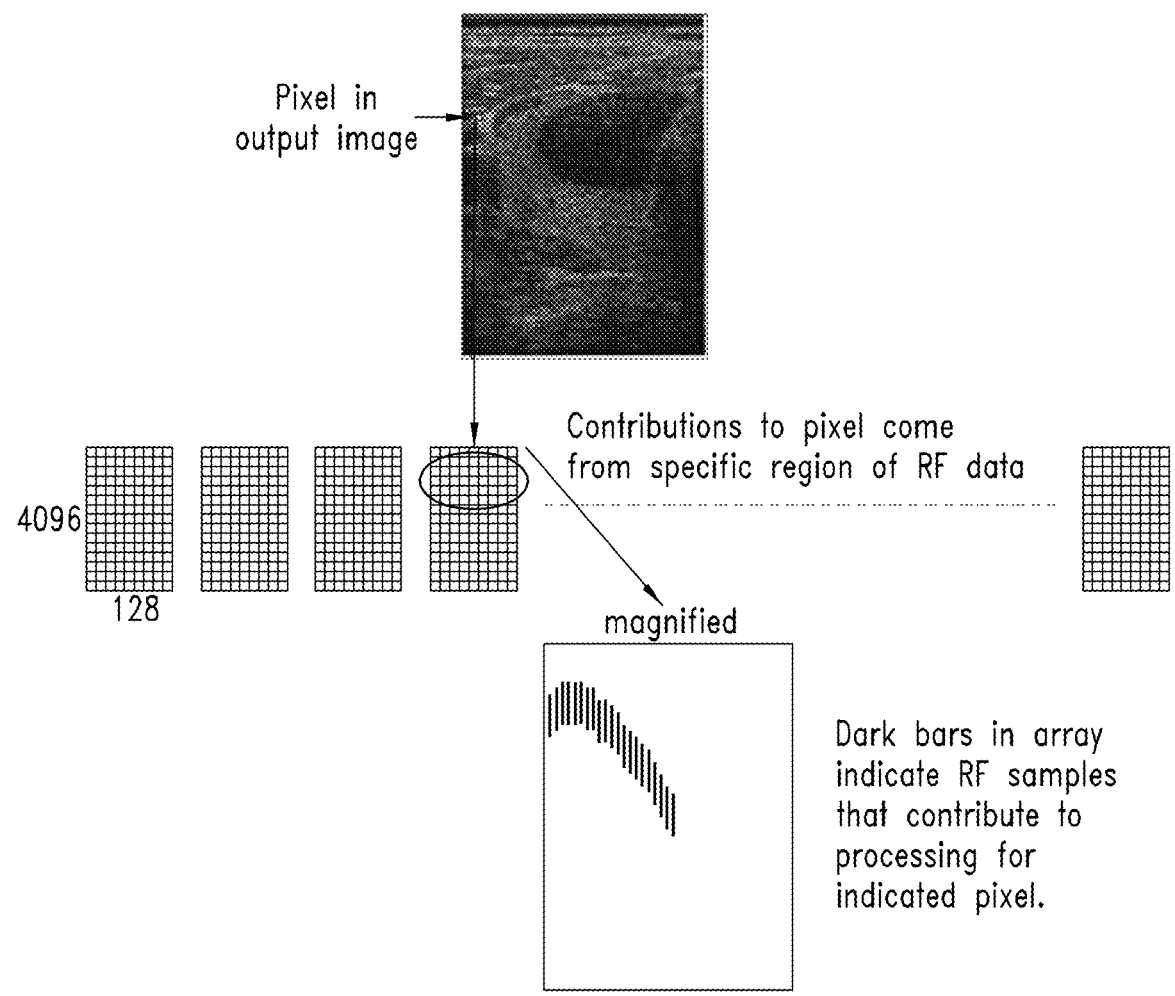
FIG. 11 is an illustration of a pixel mapping process used in pixel-oriented processing.

We next consider the processing strategy for a single pixel of our ultrasound image. In this discussion, we will assume that our objective is to obtain the echo intensity at the corresponding spatial location of the pixel with respect to the transducer array. Other acoustic parameters may be similarly obtained. Our first step is to find the region of acquisition RF data containing samples that contribute to the echo intensity calculation. To accomplish this for the scanning method of FIG. 10, we first find the acquisition scan line that comes closest to intersecting the pixel location, and then use the corresponding individual element data array. FIG. 11 shows this mapping process for an example pixel in an ultrasound image. In FIG. 11, the indicated pixel maps to the closest acquisition line of the scan, which in this case is scan line 4, whose RF data resides in the fourth individual element RF data array (which represents data collected from the fourth transmit/receive event). More than one RF data array could be chosen as contributing to the pixel signal, but for this example we will consider only a single data array.

Out next step is to map out the region in the individual element array containing samples that contribute to the pixel's intensity calculation. This mapping process is fairly complex and depends on several factors. The transducer elements each have a region of sensitivity that determines how they will respond to a signal returning from a particular point in the image field. For a given image point, only elements that have sensitivities above a predetermined threshold need be considered, since if the sensitivity is too low, an element will not contribute useful information to the pixel's quantity. This sensitivity threshold then determines the number of element data columns to include in the mapped region. As shown in FIG. 5, elements on the far right hand side of the transducer are not included in the mapped data region.

The starting depth of the mapped data region is determined by the arrival time of the returning echo at each individual transducer element. As shown in FIG. 11, the image point signal for elements further away from the image point is captured later in time, and so the starting point of the data set is deeper in memory. Finally, the depth range needed for the mapped data region is dependent on the duration of the transmit pulse generated. Longer transmit pulses will excite the image point for a longer period of time, generating echo signals that extend over a larger depth span of the RF memory.

Fortunately, many of the factors that go into determining the region of mapped data can be pre-computed for a given pixel grid, since this grid does not change over the multiple frames of a real-time image sequence. Using pre-computed factors, the mapped data region for a given pixel can be rapidly and efficiently determined, saving considerable computations during real-time imaging.

After selecting out the pixel mapped RF data, we can organize it into a matrix, $RFP_{nm}$, as shown below.

$$RFP_{nm} = \begin{bmatrix} a_{11} a_{12} & \cdots & a_{1k} \\ a_{21} & & \\ \cdots & & \\ \cdots & & \\ a_{j1} & \cdots & a_{jk} \end{bmatrix}$$

The notation '$P_{nm}$' refers to the image pixel in row n, column m. The matrix columns are the vertical bars of FIG. 11 where it is assumed that the number of samples, j, in each vertical bar are the same. The number of samples, j, is dependent on the range of RF data in time needed for capturing the signal generated by the transmit pulse. The index, k, is the number of channels in the RF data array that have adequate signal strength from to the image point to participate in the intensity calculation.

All U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the disclosure have been described herein for purposes of illustration, various modifications may be made without deviating from the spirit and scope of the disclosure. For example, the processing operations described above to generate pixel or voxel acoustic information have been implemented using matrix operations, but it is recognized that standard mathematical operations, or even hardware based processing methods could be used to accomplish some or all of the processing steps. Accordingly, the disclosure is not limited except as by the appended claims.

The invention claimed is:

1. A method of producing quantitative Doppler ultrasound images, comprising:
    emitting one or more emission ensembles each comprising N emissions of plane wave unfocused ultrasonic signals into a medium over at least a portion of a transducer's entire field of view, each of the one or more emission ensembles including multiple plane wave unfocused transmit and receive events at a fixed pulse repetition frequency (PRF) and steering angle, and each of the one or more emission ensembles of plane wave unfocused ultrasonic signals emitted into a same portion of the transducer's field of view in the medium with a different steering angle than other emission ensembles of the one or more emission ensembles;
    receiving and storing in a memory scattered and reflected ultrasonic signals received by a plurality of receiving elements in an array of receiving elements in the transducer in response to each of the N ultrasonic emissions, wherein the receiving of the reflected ultrasonic signals is performed in one of two ways depending upon expected blood flow velocity and minimum pulse rate frequency permitted to display peak blood velocities without aliasing, namely:
        (a) in response to a maximum depth of measurement that restricts the PRF of the emission ensembles to a maximum rate that is less than a multiple M of the rate needed to adequately sample the flow velocity Doppler frequency, collecting all N reflected ultrasonic signals of each emission ensemble at one angle and then changing angles until all angles are complete, or
        (b) in response to a maximum depth of measurement that allows acquiring acquisitions in the emission ensembles at a multiple M of the rate required to sample the flow velocity Doppler frequency, collecting one reflected ultrasonic signal for each of M angles and then repeating for N reflected ultrasonic signals;
    processing the stored received ultrasonic signals with respect to each image point of a displayable set of image points within the same portion of the transducer's field of view to extract quantitative motion information from points in the medium corresponding to the at least one image point, including processing each image point with a respective subset of the same stored scattered and reflected ultrasonic signals acquired from the multiple ultrasonic emissions; and
    generating on a display device a two-dimensional parametric image with respect to each image point that is derived from the quantitative motion information.

2. The method of claim 1, wherein the image point of the displayable set of image points is an image pixel and the processing includes processing the respective subset of the received and stored scattered and reflected ultrasonic signals in real time using a pixel-oriented processing method that comprises:
    generating a set of image pixels chosen to represent an area in the medium to be displayed on the display device that is in the field of view of the transducer receiving the scattered and reflected ultrasonic signals, in which every image pixel in the set of image pixels has a known spatial relationship to the plurality of receiving elements;
    mapping the image pixels into regions of the stored ultrasonic signals;
    organizing the mapped regions of the stored ultrasonic signals into arrays for the image pixels;
    reconstructing of amplitude and phase of the stored ultrasonic signals from at least a subset of the stored ultrasonic signals at each image pixel location in the area;
    processing at least one ensemble of transmit-receive events, which comprises at least one emission of a timed sequence of ultrasonic signals and receiving and storing of the scattered and reflected ultrasonic signals, to derive estimated Doppler parameters of the media motion at each image pixel location in the area; and
    producing an image on the display device of one or more of the derived estimated Doppler parameters at each image pixel location in the area to be displayed in the image.

3. The method of claim 2 wherein the parameters relate to fluid flow or tissue motion.

4. The method of claim 2, where the ensembles of the multiple unfocused ultrasonic signals are varied in such a way as to provide multiple angles of propagation into the medium, insonifying spatial locations from multiple angles, and the Doppler parameter estimates from the multiple angles of propagation are processed to compute velocity vectors at each of the image pixel locations.

5. The method of claim 2, where the ensembles of the multiple unfocused ultrasonic signals are varied in such a way as to provide multiple angles of propagation into the medium, insonifying spatial locations from multiple angles, and the Doppler parameter estimates from the multiple angles of propagation are processed to discriminate between true velocity in the medium and acoustic or electrical noise.

6. The method of claim 2, where the ensembles of the multiple unfocused ultrasonic signals are varied in such a way as to provide multiple angles of propagation into the medium, insonifying spatial locations from multiple angles, and the Doppler parameter estimates from the multiple angles of propagation are processed to compute Doppler power at each of the image pixel locations.

7. The method of claim 2 wherein the accuracy of the Doppler parameter estimates is adjusted by changing the number of ultrasonic signals.

8. The method of claim 2 wherein the processing comprises using Doppler frequency shift spectral analysis to derive the Doppler parameters of media motion at each of the image pixel locations.

9. The method of claim 8 wherein a derived Doppler parameter of media motion comprises maximum velocity.

10. The method of claim 8 wherein a derived Doppler parameter of media motion comprises velocity variance as an indicator of turbulent flow in the medium.

11. The method of claim 8 wherein the derived Doppler parameters of the media motion comprise at least one parameter from among the mode, the mean, the variance, the maximum, the power in a spectral band, and the spectral analysis further comprises error estimates for the derived parameters.

12. The method of claim 8 wherein the accuracy of the derived parameters is adjusted by changing the number of transmit-receive events in the ensemble.

13. The method of claim 8 wherein processing of the ensembles comprises producing and displaying in real time the Doppler parameter estimates for at least one image pixel location without reducing a rate of acquisition of Doppler frames.

14. The method of claim 8 wherein emitting comprises emitting the ensembles of the multiple unfocused ultrasonic signals that are varied to provide multiple directional angles M of propagation into the medium, and processing comprises using the Doppler parameter estimates from the multiple directional angles to compute velocity vectors at each of the image pixel locations.

15. The method of claim 8 wherein emitting comprises emitting multiple unfocused ultrasonic signals that are varied to provide multiple directional angles of propagation into the medium, and processing comprises using the Doppler parameter estimates from the multiple directional angles to discriminate between data resulting from true motion in the medium and data resulting from acoustic or electrical noise.

16. The method of claim 8 wherein producing an image includes post-processing the stored received ultrasonic data to produce image frames that display derived motion parameters of the medium as an image or as a movie sequence of image frames.

17. The method of claim 2 wherein producing an image comprises producing an image or time sequence of images that display values of a derived parameter over an entire field of view of the transducer array.

18. The method of claim 2 wherein producing an image comprises producing multiple frames of the image that display motion parameters of the medium as a movie sequence of two-dimensional images.

19. The method of claim 2 wherein the Doppler parameters comprise at least one from among:
a peak velocity corresponding to the Doppler shift frequency with greatest power;
a maximum velocity corresponding to a maximum Doppler shift frequency for a particular minimum power threshold;
a velocity variance as an indicator of turbulent flow of the medium; and
a velocity vector direction variance as an indicator of turbulent flow of the medium.

20. The method of claim 2 wherein the timed sequence comprises a time interval that corresponds to one or more cardiac cycles, and producing an image comprises producing a single image for each cardiac cycle using a maximum or minimum value of a derived parameter at each pixel point, or a difference of two derived parameters at each pixel, or a ratio of two derived parameters taken at some time in the cardiac cycle.

21. The method of claim 20 wherein the derived parameters may be computed over an entire record, and are selected for display at particular phases of clinical significance in the cardiac cycle, including systole and diastole, or intervals of strong turbulence, or any time of interest visualized by the displayed image.

22. A system for generating quantitative Doppler ultrasound images, comprising:
a module comprising a transducer capable of emitting one or more emission ensembles of plane wave unfocused ultrasonic signals into a medium over at least a portion of a transducer's entire field of view, each of the one or more emission ensembles including multiple plane wave unfocused transmit and receive events at a fixed pulse repetition frequency (PRF) and steering angle, and each of the one or more emission ensembles comprising N emissions of plane wave unfocused ultrasonic signals emitted into a same portion of the transducer's field of view in the medium with a different steering angle than other emission ensembles of the one or more emission ensembles, and further capable of receiving and storing reflected ultrasonic signals received by a plurality of receiving elements in an array of receiving elements in the transducer in response to each of the N ultrasonic emissions, the receiving of the reflected ultrasonic signals is performed in one of two ways depending upon expected blood flow velocity and minimum pulse rate frequency permitted to display peak blood velocities without aliasing, namely:
(a) in response to a maximum depth of measurement that restricts the PRF of the emission ensembles to a maximum rate that is less than a multiple M of the rate needed to adequately sample the flow velocity Doppler frequency, collecting all N reflected ultrasonic signals of each emission ensemble at one angle and then changing steering angles until all steering angles are complete, or
(b) in response to a maximum depth of measurement that allows acquiring acquisitions in the emission ensembles at a multiple M of the rate required to sample the flow velocity Doppler frequency, collecting one reflected ultrasonic signal for each of M steering angles and then repeating for N reflected ultrasonic signals; and
a processor coupled to the transducer and capable of receiving the stored ultrasonic signals with respect to each image point of a displayable set of image points to extract quantitative motion information from points in the medium corresponding to each image point, including processing each image point in the displayable set of image points with a respective subset of the same stored scattered and reflected ultrasonic signals acquired from the multiple emissions of unfocused ultrasonic, and generating on the display device a two-dimensional parametric image with respect to each image point that is derived from the quantitative motion information.

23. The system of claim 22 wherein the image point to be displayed on the display device is an image pixel and wherein the processor is configured to process in real time the respective subset of the received and stored reflected ultrasonic signals by using a pixel-oriented processing method that comprises:

generating a set of image pixels chosen to represent an area in the medium to be displayed on the display device that is in the field of view of the transducer receiving the ultrasonic signals, in which every image pixel in the set of image pixels has a known spatial relationship to the plurality of receiving elements;

mapping the image pixels into regions of the stored ultrasonic signals;

organizing the mapped regions of the stored ultrasonic signals into arrays for the image pixels;

reconstructing of amplitude and phase of the received reflected ultrasonic signals from at least a subset of the received reflected ultrasonic signals at each image pixel location in the area;

processing at least one ensemble of transmit-receive events, which ensemble comprises at least one emission of a timed sequence of ultrasonic signals and receiving and storing of the reflected ultrasonic signals in response thereto, to derive estimated Doppler parameters of the media motion at each image pixel location in the area; and producing an image on a display device of the one or more derived estimated Doppler parameters at each image pixel location in the area displayed in the image.

24. The system of claim 23 wherein the ensembles of multiple unfocused ultrasonic signals are varied in such a way as to provide multiple angles of propagation into the medium, and the Doppler parameter estimates from the multiple angles of propagation are processed to compute velocity vectors at each of the image pixel locations.

25. The system of claim 23, where the ensembles of multiple unfocused ultrasonic signals are varied in such a way as to provide multiple angles of propagation into the medium, and the Doppler parameter estimates from the multiple angles of propagation are processed to discriminate between true velocity in the medium and acoustic or electrical noise.

26. The system of claim 23, where the ensembles of multiple unfocused ultrasonic signals are varied in such a way as to provide multiple angles of propagation into the medium, and the Doppler parameter estimates from the multiple angles of propagation are processed to compute Doppler power at each of the image pixel locations.

27. The method of claim 23 wherein the accuracy of the Doppler parameter estimates is adjusted by changing the number of ultrasonic signals.

28. The system of claim 23 wherein the processing comprises using Doppler frequency shift spectral analysis to derive the Doppler parameters of media motion at each of the image pixel locations.

29. The system of claim 28 wherein a derived Doppler parameter of media motion comprises maximum velocity.

30. The system of claim 28 wherein a derived Doppler parameter of media motion comprises velocity variance as an indicator of turbulent flow in the medium.

31. The system of claim 28 wherein the derived Doppler parameters of the media motion comprise at least one parameter from among the mode, the mean, the variance, the maximum, the power in a spectral band, and the spectral analysis further comprises error estimates for the derived parameters.

32. The system of claim 28 wherein the accuracy of the derived parameters is adjusted by changing the number of transmit-receive events in the ensemble.

33. The system of claim 28 wherein processing of the ensembles comprises producing and displaying on the display device in real time the Doppler parameter estimates for at least one image pixel location without reducing the rate of acquisition of Doppler frames.

34. The system of claim 28 wherein emitting comprises emitting the ensembles of multiple unfocused ultrasonic signals from the transducer to provide multiple directional angles of propagation into the medium from the transducer, and the processing comprises using the Doppler parameter estimates from the multiple directional angles in the processor to compute velocity vectors at each of the image pixel locations.

35. The system of claim 28 wherein emitting comprises emitting the ensembles of multiple unfocused ultrasonic signals to provide multiple directional angles of propagation from the transducer into the medium, and processing comprises using the Doppler parameter estimates from the multiple directional angles in the processor to discriminate between data resulting from true motion in the medium and data resulting from acoustic or electrical noise.

36. The system of claim 28 wherein emitting comprises emitting the ensembles of multiple unfocused ultrasonic signals to provide multiple directional angles of propagation from the transducer into the medium, and processing comprises using the Doppler parameter estimates from the multiple directional angles in the processor to compute absolute (angle-corrected) values of spectral parameters including the mode, the mean, the variance and the maximum power in a spectral band at each of the image pixel locations.

37. The system of claim 23 wherein producing an image comprises producing an image or time sequence of images on the display device that display values of a derived parameter over an entire field of view of the transducer array.

38. The system of claim 23 wherein producing an image comprises producing multiple frames of the image that display motion parameters of the medium on the display device as a movie sequence of two-dimensional images.

39. The system of claim 23 wherein the Doppler parameters comprise at least one from among:

a peak velocity corresponding to the Doppler shift frequency with greatest power;

a maximum velocity corresponding to a maximum Doppler shift frequency for a particular minimum power threshold;

a velocity variance as an indicator of turbulent flow of the medium; and a velocity vector direction variance as an indicator of turbulent flow of the medium.

40. The system of claim 23 wherein the timed sequence comprises a time interval that corresponds to one or more cardiac cycles, and producing an image comprises producing a single image for each cardiac cycle using a maximum or minimum value of a derived parameter at each pixel point, or a difference of two derived parameters at each pixel, or a ratio of two derived parameters taken at some time in the cardiac cycle.

41. The system of claim 40 wherein the derived parameters may be computed over an entire record, and are selected for display at particular phases of clinical significance in the cardiac cycle, including systole and diastole, or intervals of strong turbulence, or any time of interest visualized by the displayed image.

42. A method of producing quantitative Doppler ultrasound images, comprising:
  emitting one or more emission ensembles each comprising N emissions of plane wave unfocused ultrasonic signals into a medium over at least a portion of a transducer's entire field of view, each of the one or more emission ensembles including multiple plane wave unfocused transmit and receive events at a fixed pulse repetition rate (PRF) and steering angle, and each of the one or more emission ensembles of plane wave unfocused ultrasonic signals emitted into a same portion of the transducer's field of view in the medium with a different steering angle than other emission ensembles of the one or more emission ensembles;
  receiving and storing in a memory reflected ultrasonic signals received by a plurality of receiving elements in an array of receiving elements in the transducer in response to each of the N ultrasonic emissions, wherein the receiving of the reflected ultrasonic signals is performed in one of two ways depending upon expected blood flow velocity and minimum pulse rate frequency permitted to visually display peak blood velocities without aliasing, namely:
    (a) in response to a maximum depth of measurement that restricts the PRF of the emission ensembles to a maximum rate that is less than a multiple M of the rate needed to adequately sample the flow velocity Doppler frequency, collecting all N reflected ultrasonic signals of each emission ensemble at one angle and then changing angles until all angles are complete, or
    (b) in response to a maximum depth of measurement that allows acquiring acquisitions in the emission ensembles at a multiple M of the rate required to sample the flow velocity Doppler frequency, collecting one reflected ultrasonic signal for each of M angles and then repeating for N reflected ultrasonic signals;
  processing the stored received ultrasonic signals with respect to at least one image point to extract quantitative motion information from points in the medium corresponding to the at least one image point, the processing including processing each image point with a respective subset of the received and stored reflected ultrasonic signals in real time using a pixel-oriented processing method that includes:
    choosing a set of image pixels in a display device to represent an area in the medium to be displayed on a display device that is in the field of view of the transducer receiving the reflected ultrasonic signals, in which every image pixel in the set of image pixels has a known spatial relationship to the plurality of receiving elements in the transducer;
    mapping each image pixel into regions of the stored ultrasonic signals;
    organizing the mapped regions of the stored ultrasonic signals into arrays for each image pixel;
    using matrix processing at each image pixel location in the area to be displayed to reconstruct amplitude and phase of the received scattered ultrasonic signals from at least a subset of the stored ultrasonic signals;
    processing at least one emission ensemble of transmit-receive events, which emission ensemble includes at least one emission of a timed sequence of ultrasonic signals and receiving and storing of the reflected ultrasonic signals, to derive one or more estimated Doppler parameters of media motion at each image pixel location in the area to be displayed; and
    producing on the display device a two-dimensional parametric image derived from the quantitative motion information of the one or more estimated Doppler parameters used in generating the display at each image pixel location in the area to be displayed.

43. The method of claim 42 wherein the parameters relate to fluid flow or tissue motion.

44. The method of claim 42, where the ensembles of multiple unfocused ultrasonic signals are varied in such a way as to provide multiple angles of propagation into the medium, and the Doppler parameter estimates from the multiple angles of propagation are processed to compute velocity vectors at each of the image pixel locations.

45. The method of claim 42, where the ensembles of multiple unfocused ultrasonic signals are varied in such a way as to provide multiple angles of propagation into the medium, and the Doppler parameter estimates from the multiple angles of propagation are processed to discriminate between true velocity in the medium and acoustic or electrical noise.

46. The method of claim 42, where the ensembles of multiple unfocused ultrasonic signals are varied in such a way as to provide multiple angles of propagation into the medium, and the Doppler parameter estimates from the multiple angles of propagation are processed to compute Doppler power at each of the image pixel locations.

47. The method of claim 42 wherein the accuracy of the Doppler parameter estimates is adjusted by changing the number of ultrasonic signals.

48. The method of claim 42 wherein the processing comprises using Doppler frequency shift spectral analysis to derive the Doppler parameters of media motion at each of the image pixel locations.

49. The method of claim 48 wherein a derived Doppler parameter of media motion comprises maximum velocity.

50. The method of claim 48 wherein a derived Doppler parameter of media motion comprises velocity variance as an indicator of turbulent flow in the medium.

51. The method of claim 48 wherein the derived Doppler parameters of the media motion comprise at least one parameter from among the mode, the mean, the variance, the maximum, the power in a spectral band, and the spectral analysis further comprises error estimates for the derived parameters.

52. The method of claim 48 wherein the accuracy of the derived parameters is adjusted by changing the number of transmit-receive events in the ensemble.

53. The method of claim 48 wherein processing of the emission ensembles comprises producing and displaying in real time the Doppler parameter estimates for at least one image pixel location without reducing a rate of acquisition of Doppler frames.

54. The method of claim 48 wherein emitting the ensembles of multiple ultrasonic signals comprises emitting ensembles of multiple unfocused ultrasonic signals that are varied to provide multiple directional angles of propagation into the medium, and processing comprises using the Doppler parameter estimates from the multiple directional angles to compute velocity vectors at each of the image pixel locations.

55. The method of claim 48 wherein emitting the ensembles of multiple unfocused ultrasonic signals comprises emitting ensembles of multiple unfocused ultrasonic signals that are varied to provide multiple directional angles of propagation into the medium, and processing comprises using the Doppler parameter estimates from the multiple directional angles to discriminate between data resulting from true motion in the medium and data resulting from acoustic or electrical noise.

56. The method of claim 48 wherein emitting the ensembles of multiple unfocused ultrasonic signals comprises emitting ensembles of multiple unfocused ultrasonic signals that are varied to provide multiple directional angles of propagation into the medium, and processing comprises using the Doppler parameter estimates from the multiple directional angles to compute absolute (angle-corrected) values of spectral parameters including the mode, the mean, the variance and the maximum power in a spectral band at each of the image pixel locations.

* * * * *